US011851677B2

(12) United States Patent
Parone et al.

(10) Patent No.: US 11,851,677 B2
(45) Date of Patent: Dec. 26, 2023

(54) COMPOSITION AND METHODS FOR INDUCING MYELOID SUPPRESSIVE CELLS AND USE THEREOF

(71) Applicant: FATE THERAPEUTICS, INC., San Diego, CA (US)

(72) Inventors: Philippe A. Parone, San Diego, CA (US); Robert S. Tacke, San Diego, CA (US); Bahram Valamehr, San Diego, CA (US); Daniel Shoemaker, San Diego, CA (US); Martin Hosking, San Diego, CA (US); Lisa Guerrettaz, San Diego, CA (US)

(73) Assignee: Fate Therapeutics, Inc.

( * ) Notice: Subject to any disclaimer, the term of this patent is extended or adjusted under 35 U.S.C. 154(b) by 664 days.

(21) Appl. No.: 16/622,237

(22) PCT Filed: Jun. 13, 2018

(86) PCT No.: PCT/US2018/037286
§ 371 (c)(1),
(2) Date: Dec. 12, 2019

(87) PCT Pub. No.: WO2018/231951
PCT Pub. Date: Dec. 20, 2018

(65) Prior Publication Data
US 2020/0102536 A1    Apr. 2, 2020

Related U.S. Application Data

(60) Provisional application No. 62/519,123, filed on Jun. 13, 2017.

(51) Int. Cl.
| | |
|---|---|
| A61K 35/15 | (2015.01) |
| A61K 35/44 | (2015.01) |
| C12N 5/078 | (2010.01) |

(52) U.S. Cl.
CPC ............ *C12N 5/0634* (2013.01); *A61K 35/15* (2013.01); *A61K 35/44* (2013.01);
(Continued)

(58) Field of Classification Search
CPC ............. C12N 5/0634; C12N 2500/02; C12N 2501/115; C12N 2501/125;
(Continued)

(56) References Cited

U.S. PATENT DOCUMENTS

2016/0186137 A1   6/2016   Thomson et al.
2017/0152481 A1*   6/2017   Lanza ..................... A61P 9/10
(Continued)

FOREIGN PATENT DOCUMENTS

WO    WO-2010/062990 A1    6/2010

OTHER PUBLICATIONS

Tan et al ("Disruption of CCR5-Dependent Homing of Regulatory T Cells Inhibits Tumor Growth in a Murine Model of Pancreatic Cancer," J Immunol 2009; 182:1746-1755) (Year: 2009).*
(Continued)

*Primary Examiner* — Anoop K Singh
*Assistant Examiner* — Suzanne E Ziska
(74) *Attorney, Agent, or Firm* — Greenberg Traurig, LLP

(57) ABSTRACT

Compositions and methods for manufacturing induced immune regulatory cells comprising induced myeloid suppressive cells including MDSCs (myeloid-derived suppressor cells), dendritic cells, macrophages, and subpopulations thereof are provided. Also provided are methods and compositions for further modifying and modulating the induced immune regulatory cells to achieve enhanced therapeutic potential in treating autoimmune disorders, hematological malignancies, solid tumors, viral infections, neurodegenerative disorders, inflammatory conditions, or GvHD.

12 Claims, 11 Drawing Sheets

(52) U.S. Cl.
CPC .... *C12N 2500/02* (2013.01); *C12N 2501/115* (2013.01); *C12N 2501/125* (2013.01); *C12N 2501/155* (2013.01); *C12N 2501/165* (2013.01); *C12N 2501/2306* (2013.01); *C12N 2501/2311* (2013.01); *C12N 2501/26* (2013.01); *C12N 2501/727* (2013.01); *C12N 2502/11* (2013.01); *C12N 2506/45* (2013.01); *C12N 2510/00* (2013.01); *C12N 2533/50* (2013.01)

(58) Field of Classification Search
CPC ........ C12N 2501/155; C12N 2501/165; C12N 2501/2306; C12N 2501/231126; C12N 2501/727; C12N 2502/11; C12N 2506/45; C12N 2510/00; C12N 2533/50; A61K 35/15; A61K 35/44
See application file for complete search history.

(56) References Cited

U.S. PATENT DOCUMENTS

| | | | |
|---|---|---|---|
| 2018/0072992 A1 | 3/2018 | Valamehr et al. | |
| 2018/0282762 A1* | 10/2018 | Gori | A61K 35/545 |
| 2018/0296603 A1* | 10/2018 | Gori | C12N 5/0647 |

OTHER PUBLICATIONS

Clements, V.K. et al. (Mar. 2018, e-published Jan. 3, 2018). "Frontline Science: High fat diet and leptin promote tumor progression by inducing myeloid-derived suppressor cells," *J Leukov Biol* 103(3):395-407.
Ditadi, A. et al. (May 2015, e-published Apr. 27, 2015). "Human definitive haemogenic endothelium and arterial vascular endothelium represent distinct lineages," *Nat Cell Biol* 17(5):580-591.
Ditadi, A. et al. (May 15, 2016, e-published Oct. 9, 2015). Directed differentiation of definitive hemogenic endothelium and hematopoietic progenitors from human pluripotent stem cells, *Methods* 101:65-72.
Esteban, M.A. et al. (Jan. 8, 2010, e-published Dec. 1, 2009). "Vitamin C enhances the generation of mouse and human induced pluripotent stem cells," *Cell Stem Cell* 6(10):71-79.
Feng, B. et al. (Apr. 3, 2009). "Molecules that promote or enhance reprogramming of somatic cells to induced pluripotent stem cells," *Cell Stem Cell* 4(4):301-312.
Huangfu, D. et al. (Jul. 2008, e-published Jun. 22, 2008). "Induction of pluripotent stem cells by defined factors is greatly improved by small-molecule compounds," *Nat Biotechnol* 26(7):795-797.
Huangfu, D. et al. (Nov. 2008, e-published Oct. 12, 2008). "Induction of pluripotent stem cells from primary human fibroblasts with only Oct4 and Sox2," *Nat Biotechnol* 26(11):1269-1275.
Ichida, J.K. et al. (Nov. 6, 2009, e-published Oct. 8, 2009). "A small-molecule inhibitor of tgf-ß signaling replaces sox2 in reprogramming by inducing nanog," *Cell Stem Cell* 5(5):491-503.
International Search Report dated Oct. 4, 2018, for PCT Application No. PCT/US2018/037286, filed Jun. 13, 2018, 4 pages.
Kennedy, M. et al. (Dec. 27, 2012, e-published Dec. 7, 2012). "T lymphocyte potential marks the emergence of definitive hematopoietic progenitors in human pluripotent stem cell differentiation cultures," *Cell Rep* 2(6):1722-1735.
Kim, D. et al. (Jun. 5, 2009, e-published May 28, 2009). "Generation of human induced pluripotent stem cells by direct delivery of reprogramming proteins," *Cell Stem Cell* 4(6):472-276.
Knorr, D.A. et al. (Apr. 2013, e-published Mar. 20, 2013). "Clinical-scale derivation of natural killer cells from human pluripotent stem cells for cancer therapy," *Stem Cells Transl Med* 2(4):274-283.
Lyssiotis, C.A. et al. (Jun. 2, 2009, e-published May 15, 2009). "Reprogramming of murine fibroblasts to induced pluripotent stem cells with chemical complementation of Klf4," *PNAS USA* 106(22):8912-8917.
Maherali, N. et al. (Nov. 3, 2009, e-published Sep. 17, 2009). "Tgfß signal inhibition cooperates in the induction of iPSCs and replaces Sox2 and cMyc," *Curr Biol* 19(20):1718-1723.
Saha, K. et al. (Dec. 4, 2009). "Technical challenges in using human induced pluripotent stem cells to model disease," *Cell Stem Cell* 5(6):584-595.
Shi, Y. et al. (Jun. 5, 2008). "A combined chemical and genetic approach for the generation of induced pluripotent stem cells," *Cell Stem Cell* 2(6):525-528.
Shi, Y. et al. (Nov. 6, 2008). "Induction of pluripotent stem cells from mouse embryonic fibroblasts by Oct4 and Klf4 with small-molecule compounds," *Cell Stem Cell* 3(5):568-574.
Silva, J. et al. (Oct. 21, 2008). "Promotion of reprogramming to ground state pluripotency by signal inhibition," *PloS Biol* 6(10):e253.
Takahashi, K. et al. (Aug. 25, 2006, e-published Aug. 10, 2006). "Induction of pluripotent stem cells from mouse embryonic and adult fibroblast cultures by defined factors," *Cell* 126(4):663-676.
Takahashi, K. et al. (Nov. 30, 2007). "Induction of pluripotent stem cells from adult human fibroblasts by defined factors," *Cell* 131(5):861-872.
Written Opinion dated Oct. 4, 2018, for PCT Application No. PCT/US2018/037286, filed Jun. 13, 2018, 4 pages.
Yamanaka, S. et al. (Jul. 2, 2009). "Elite and stochastic models for induced pluripotent stem cell generation," *Nature* 460(7251):49-52.
Yu, J. et al. (Dec. 21, 2007, e-published Nov. 20, 2007). "Induced pluripotent stem cell lines derived from human somatic cells," *Science* 318(5858):1917-1920.
Zhou, H. et al. (May 8, 2009, e-published Apr. 23, 2009). "Generation of induced pluripotent stem cells using recombinant proteins," *Cell Stem Cell* 4(5):381-384.

* cited by examiner

| | MDSC (% non adherent cells ± SEM) |
|---|---|
| CD45+ | 95.15 ± 1.57 |
| CD45+CD33+ | 93.75 ± 1.77 |
| Monocytic MDSC (CD45+CD33+CD14+) | 52.8 ± 8.93 |
| PDL1 expression (CD45+PDL1+) | 56.66 ± 9.297 |
| Granulocytes (CD45+CD33+CD66b+) | 3.833 ± 2.19 |
| Erythrocytes (CD45-CD235+) | 0.084 ± 0.05 |
| Lymphoid (CD45+CD7+) | 0.015 ± 0.01 |

COMPOSITION AND METHODS FOR INDUCING MYELOID SUPPRESSIVE CELLS AND USE THEREOF

RELATED APPLICATION

This application claims priority to U.S. Provisional Application Ser. No. 62/519,123, filed Jun. 13, 2017, the disclosure of which is hereby incorporated by reference in its entirety.

FIELD OF THE INVENTION

The present disclosure is broadly concerned with the field of adoptive immune cell therapies. More particularly, the invention relates to improved culture platforms for manufacturing derivative regulatory immune cells of myeloid lineage suitable for adoptive cell therapies from pluripotent stem cells including human induced pluripotent stem cells.

BACKGROUND OF THE INVENTION

Adoptive immunotherapy involves administration of immune cells to patients having tumors, cancers, immune disorders, or infections, whereby the administered immune cells provide a therapeutic benefit to the patients. Generally speaking, immune cells suitable for immunotherapy include, but are not limited to, B cells, T cells, Natural Killer (NK) cells, NKT (Natural Killer T) cells, and hematopoietic stem or progenitor cells. In addition, immune regulatory cells, such as myeloid-derived suppressor cells (MDSCs), macrophages and dendritic cells, are potent immune regulators of NK, B, and T cell, and are of particular interest in regulating immune responses in cell therapies. Mediating complete and durable disease responses in patients is the central goal of these cell-based immunotherapies.

MDSCs are potent immune-regulators of Natural Killer, B and T cells. Suppression of T cell effector function occurs through multiple mechanisms, including, but not limited to: PD-L1/PD1 mediated anergy, arginase 1-mediated depletion of L-arginine, inducible nitric oxide synthase and NADPH oxidase production of free radical species, indoleamine 2,3-dioxygenase sequestration of cysteine, and the expansion of T-regulatory cells. The immunoregulatory potency of MDSCs is underscored by the key role of MDSCs in promoting the immunosuppressive microenvironment of solid tumors. These properties suggest that MDSCs could serve as an effective cell therapy to restore immune tolerance for the treatment of immune disorders, including Graft-versus-host-disease (GvHD). In several murine disease models including GvHD, Inflammatory Bowel Disorder, Type 1 Diabetes, Systemic Lupus Erythematosus and Multiple Sclerosis, exogenously delivered MDSCs were shown to attenuate immune-related pathogenesis. However, developing patient derived MDSCs for the treatment of immune disorders faces several challenges, including paucity and heterogeneity of MDSCs, poor scalability, high cost of manufacturing and limited options for genetic engineering to enhance therapeutic attributes.

A major hurdle in utilizing hiPSCs and derivative cells including MDSCs, among other immune regulatory cells, for therapeutic purposes has been the requirement to initially co-culture such cells with murine- or human-derived stromal cells in the presence of ill-defined serum-containing media in order to maintain pluripotency and induce differentiation. In addition, the existing protocols have also employed a strategy consisting of culturing iPSC to form an embryoid body (EB), which is a heterogeneous aggregate of cells comprising various differentiated cells including ectoderm, mesoderm, and endoderm cells. Those procedures either require aggregating pluripotent cells by, for example, spinning to form clumps, allowing the cells to settle and aggregate in wells or allowing for passive aggregation and clump formation in suspension culture. The formed EBs are maintained for certain duration in differentiation inducing culture systems, typically seven to ten days, to allow for proper differentiation, then the EBs are either transferred to adherent culture for further maturation or dissociated into single cells for cell type selection in order to proceeding to the subsequent differentiation steps. (Kennedy et al., Cell Reports 2012:1722-1735; Knorr, et al., Stem Cells Translational Medicine 2013 (2):274-283). For example, Kennedy et al. teach to generate EBs for iPSCs differentiation, where pluripotent cells were treated with collagenase and trypsin to allow for scraping of the cells to form small aggregates which were then cultured to form EBs. EB formation has been shown to facilitate pluripotent stem cell differentiation, however the requirement of forming aggregates and subsequent EBs is labor intensive, the cell numbers minimally increase in this process, the cellular content in the three dimensional EB aggregates are exposed to the media factors inconsistently and unevenly, which leads to heterogeneous derivative cells that are in variable differentiation stages, and greatly hinders the scalability and reproducibility of a manufacturing process that is required to be efficient, consistent, and streamlined.

Additionally, since the final state of the cells, or specifically, the cell subtypes, going into the patient can be defined in large part by the manufacturing process, the importance of that process cannot be overstated. Preferentially maintaining or expanding cell subpopulations having a desired differentiation state, and/or adaptive immune cell characteristics could be extremely beneficial for enhancing the efficacy of cell-based therapies. Improved cell manufacturing processes have multiple potential advantages including decreased time to dose, increased cellular uniformity, or an increased percentage of patients that reach the desired dose. In addition, functional improvements to the cells during the manufacturing process such as homing, increased persistence and reduced toxicities may also lead to improved cell therapies. Thus, a manufacturing approach that can enhance the desired immune cell subsets both in quantity and quality could provide a significant enhancement of their therapeutic efficacy.

There is a substantial need in the art for immune cell subsets with improved therapeutic efficacy, and the need for methods and compositions of differentiating stem cell to manufacture the desired immune cells without relying on co-culturing or serum-containing media, and without requiring the formation of embryoid body aggregates as intermediates. The methods and compositions of the present invention addresses these needs and provide other related advantages in the field of immune cell therapy, and specifically in the aspect of immune regulatory cells.

SUMMARY OF THE INVENTION

MDSCs (myeloid-derived suppressor cells) in the peripheral blood of heathy patients are absent or extremely rare. Although under certain conditions, they can be generated in limited amounts from PBMCs (peripheral blood mononuclear cells) or CD34 cells through a differentiation process from early myeloid progenitors, these methods, however, do not produce sufficient numbers of MDSCs for adoptive cell therapy. The present application provides a method of producing clinically relevant number of MDSCs. Specifically, the present application provides compositions and methods for manufacturing induced immune regulatory cells comprising induced myeloid suppressive cells, which include, but are not limited to induced MDSCs (iMDSCs) and subpopulations thereof; induced dendritic cells; and induced macrophages. Also provided are methods and compositions for further modifying and modulating the induced immune regulatory cells to achieve enhanced therapeutic potential in treating conditions such as autoimmune disorders, hematological malignancies, solid tumors, viral infections, neurodegenerative diseases, inflammatory conditions and diseases, or GvHD.

One aspect of the present invention provides a method of generating a population of induced immune regulatory cells with enhanced therapeutic potential, and the method generally comprises obtaining induced definitive hemogenic endothelium cells (iHE); and directing differentiation of iHE with a medium composition comprising a ROCK inhibitor and MCSF, and optionally, GMCSF, thereby generating a population of immune regulatory cells comprising induced myeloid suppressive cells. In some embodiments, the induced myeloid suppressive cells comprise induced myeloid-derived suppressor cells (iMDSCs), induced macrophages, and/or induced dendritic cells. In some embodiments, the iMDSCs further comprise different subtypes comprising monocytic MDSCs, granulocytic MDSCs, and/or early-stage MDSCs.

In one embodiment of the method, the medium composition further comprises (1) one or more growth factors and cytokines selected from the group consisting of IL1b, IL3, IL6, IL4, IL10, IL13, TGFβ, bFGF, VEGF, SCF, and FLT3L, and optionally, one or both of an AhR antagonist and a prostaglandin pathway agonist. In one embodiment, the medium composition for generating a population of iMDSCs as disclosed herein comprises a ROCK inhibitor, MCSF, IL3, VEGF, bFGF, SCF, and FLT3L. In some embodiments, the medium comprising a ROCK inhibitor, MCSF, IL3, VEGF, bFGF, SCF, and FLT3L, further comprises one or more of IL1b, IL6, IL10, and TGFβ. In some embodiments, the medium composition does not have IL6. In some embodiments, the medium composition does not require TPO. In some embodiments, the medium composition further comprises feeder cell or feeder cell components. In some embodiments, the feeder cells are OP9. In some embodiments, the feeder cells are K562. In some embodiments, the feeder cell overexpresses one or more cytokines, ligands or receptors that support the differentiation, expansion, and/or functionality of the derivative cells. In one embodiment of the method, the medium composition is feeder-free, and/or serum-free.

In one embodiment of the method, the population of induced immune regulatory cells comprise induced myeloid-derived suppressor cells (iMDSCs); induced dendritic cells; or induced macrophages. In another embodiment of the method, the population of induced immune regulatory cells comprise one or more of: (i) CD45$^+$ cells; (ii) CD45$^+$CD33$^+$ cells; (iii) monocytic MDSCs (M-MDSCs); (iv) CD45$^+$CD33$^+$CD14$^+$ cells; (v) CD45$^+$CD33$^+$PDL1$^+$ cells; (vi) granulocytic MDSCs (G-MDSCs); (vii) CD45$^+$CD14$^-$CD15$^+$CD11b$^+$ cells; (viii) CD45$^+$CD206$^+$ cells; and (ix) CD45$^+$CD11c$^+$CD14$^-$HLADR$^{high}$ cells. In still another embodiment of the method, the population of induced immune regulatory cells comprise one or more of: (1) more than 90% of iMDSCs; (2) more than 20%, 30%, 40%, 50%, 60%, 70%, 80%, or 90% of monocytic MDSCs, and/or CD45$^+$CD33$^+$PDL1$^+$ cells; wherein the monocytic MDSCs comprise CD45$^+$CD33$^+$CD14$^+$ cells; (3) more than 20%, 30%, 40% or 50% of granulocytic MDSCs, wherein the granulocytic MDSCs comprise CD45$^+$CD11b$^+$CD14$^-$CD15$^+$ cells; (4) more than 20%, 30%, 40% or 50% of macrophages; wherein the macrophages comprise CD45$^+$CD206$^+$ cells; and (5) more than 20%, 30%, 40% or 50% of dendritic cells; wherein the dendritic cells comprise CD45$^+$CD11c$^+$CD14$^-$HLADR$^{high}$ cells. In some embodiments of the method, the obtained population of induced immune regulatory cells comprising iMDSCs is essentially free of granulocytes, erythrocytes, and/or lymphoid cells. In some embodiments, the iMDSCs comprised in the population of induced immune regulatory cells comprise one or more genetic imprints obtained from genetically engineering the iMDSCs. In one embodiment, the iMDSCs comprised in the population of induced immune regulatory cells comprise one or more genetic imprints retained from THE comprising the same genetic imprint(s).

In one embodiment of the method, the ROCK inhibitor in the medium composition is thiazovivin or Y27632. In one embodiment of the method, the AhR antagonist comprises StemRegenin1 (SR1).

In some embodiments, the obtained cells or cell population using the method has enhanced therapeutic potentials comprising one or more of (1) increased number or ratio of iMDSCs or a subpopulation thereof (M-MDSCs and/or G-MDSCs) in the induced immune regulatory cell population; (2) improved potency in suppressing T cell proliferation and effector function; and (3) ability in attenuating GvHD, as compared to MDSCs comprised in a natural setting, such as PBMC (peripheral blood mononuclear cell). In some embodiments, the obtained iMDSCs of the present application comprise significantly higher number or ratio of monocytic MDSCs or MDSCs expressing PDL1 than MDSCs comprised in a natural setting, such as PBMC, or MDSCs differentiated from primary CD34 cells isolated from PBMC.

In one embodiment of the method, the iHE cells are derived from induced pluripotent stem cells (iPSC), iPSC derived mesodermal cells, or iPSC derived mesodermal cells with definitive hemogenic endothelium potential; and optionally the iPSC comprises one or more genetic imprints retainable in its derivative cells. In some embodiments, the one or more genetic imprints of iPSC are obtained by a method comprising: (i) obtaining a source specific immune cell that is donor-, disease-, or treatment response-specific, wherein the immune cell presents retainable therapeutic attributes, and (ii) reprogramming the source specific immune cell to iPSC; or by a method comprising genomic editing during or after reprogramming a non-pluripotent cell to iPSC, wherein the genetic imprint comprises one or more genetically modified modalities introduced through genomic insertion, deletion or substitution in the genome of the iPSC.

In some embodiments, the therapeutic attributes of the source specific immune cell comprise one or more of (i) antigen targeting receptor expression; (ii) HLA presentation or lack thereof; (iii) resistance to tumor microenvironment; (iv) induction of bystander immune cells and immune modulations; (iv) improved on-target specificity with reduced off-tumor effect; (v) resistance to treatment such as chemotherapy; and (vi) improved homing, persistence, and cytotoxicity.

In some embodiments, the genetically modified modalities in the iPSCs comprise one or more of: safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the induced myeloid suppressive cells; introduced or increased expression of a chimeric receptor, a homing receptor, an anti-inflammatory molecule, an immune checkpoint protein, a cytokine/chemokine decoy receptor, a growth factor, an altered pro-inflammatory cytokine receptor, a CAR, or a surface triggering receptor for coupling with bi- or multi-specific or universal engagers; and optionally, wherein the introduced or increased expression is driven by a promoter regulated by inflammatory signaling, and/or reduced or silenced expression of a co-stimulatory gene.

In some embodiments, the chimeric receptor comprises (i) an extracellular domain comprising an antigen specific binding sequence, an immunoglobulin, or a pro-inflammatory cytokine receptor; and (ii) an intracellular domain for anti-inflammatory signaling comprising at least one of IL10R, IL35R, and AhR. In some embodiments, the genetically modified modalities comprise one or more of (i) deletion or reduced expression of B2M, TAP1, TAP2, Tapasin, NLRC5, RFXANK, CITTA, RFX5, RFXAP, or any of the HLA genes in the chromosome 6p21 region; (ii) introduced or increased expression of IDO1, PDL1, CTLA4, Arg1, IL35, IL10, HO-1, CrmB, Y136, HGFL, GMCSF, TGFβ, HLA-E, HLA-G, CAR, or surface triggering receptors for bi- or multi-specific engagers. In some other embodiments, the homing receptor or adhesion molecule comprises at least one of CXCR4, CCR2, CCR5, CCR6, CXCR3, CCR7, CD62L, and VLA4. In yet some other embodiments, the promoter is driven by the inflammatory signaling comprises TLR or IFNγR signaling; is an inducible promoter; and/or is triggered only after homing of the iMDSCs. In one embodiment, the altered pro-inflammatory cytokine receptor (i) sequesters pro-inflammatory cytokines comprising one or more of IL2R, IL6R, and IFNγR; and (ii) is membrane bound or is in a soluble form. In some embodiments, the bi- or multi-specific engager is specific to one or more tumor-specific antigen on the surface of a tumor cell.

Alternatively, in some embodiments of the method, the method further comprises genomic editing the obtained myeloid suppressive cells, including iMDSCs, through genomic insertion, deletion or substitution in the genome of the cells to introduce one or more above said genetically modified modalities to the myeloid suppressive cells. In some embodiments, the modified induced myeloid suppressive cells comprise induced myeloid-derived suppressor cells (iMDSCs), induced macrophages, and/or induced dendritic cells. In some embodiments, the modified iMDSCs further comprise different subtypes comprising monocytic MDSCs, granulocytic MDSCs, and/or early-stage MDSCs.

In some embodiments of the method, the method further comprises modulating the obtained myeloid suppressive cells with or without genetic modification by contacting the cells with one or more modulating agents to enhance therapeutic potential of the cells, including cell expansion, proliferation, persistency, homing; and/or T cell expansion and function suppression. In some embodiments, the modulated induced myeloid suppressive cells comprise induced myeloid-derived suppressor cells (iMDSCs), induced macrophages, and/or induced dendritic cells. In some embodiments, the modulated iMDSCs further comprise different subtypes comprising monocytic MDSCs, granulocytic MDSCs, and/or early-stage MDSCs.

In some embodiments of the method, the method further comprises deriving THE cells from induced pluripotent stem cells (iPSC), which step further comprises differentiating iPSCs to mesodermal cells; differentiating the derived mesodermal cells to mesodermal cells with definitive hemogenic endothelium potential, which are then differentiated hemogenic endothelium (iHE).

In one embodiment, differentiating iPSC derived mesodermal cells with definitive hemogenic endothelium potential to iHE comprises: contacting the mesodermal cells having definitive HE potential with a composition comprising bFGF and a ROCK inhibitor to obtain definitive HE cells.

In one embodiment, differentiating iPSC derived mesodermal cells to mesodermal cells with definitive hemogenic endothelium potential comprises: contacting the iPSC derived mesodermal cells with a composition comprising a BMP activator, a GSK3 inhibitor and bFGF to obtain the mesodermal cells having definitive HE potential.

In another embodiment, differentiating iPSCs to mesodermal cells comprises contacting the iPSCs with a composition comprising a BMP activator, and optionally a bFGF to obtain iPSC derived mesodermal cells.

In some embodiments of the method, the method further comprises seeding and expanding the iPSCs in a composition comprising a ROCK inhibitor, a GSK3 inhibitor and a MEK inhibitor, and the composition is free of TGFβ receptor/ALK inhibitors.

In some embodiments, the differentiation of iPSC is void of the step of generating embryoid bodies; is under monolayer culturing; is under feeder-free condition; and/or is under stromal-free condition.

Any above embodiment of the method may further comprise isolating the myeloid suppressive cells, or one or more cell types therefrom. In some embodiments, the isolated induced myeloid suppressive cells comprise induced myeloid-derived suppressor cells (iMDSCs), induced macrophages, and/or induced dendritic cells. In some embodiments, the iMDSCs further comprise different subtypes comprising monocytic MDSCs, granulocytic MDSCs, and/or early-stage MDSCs. In one embodiment, the isolated induced myeloid suppressive cells comprise MDSCs expressing PDL1.

Any above embodiment of the method may further comprise isolating the iMDSCs or subpopulations thereof, including monocytic MDSCs. In some embodiments, the isolated iMDSCs further comprise different subtypes comprising monocytic MDSCs, granulocytic MDSCs, and/or early-stage MDSCs. In some embodiments, the isolated iMDSC subpopulation comprises isolated monocytic MDSCs, isolated granulocytic MDSCs, and/or isolated early-stage MDSCs According to the various embodiments of the method illustrated above, the present invention also provides a population of induced immune regulatory cells comprising myeloid suppressive cells obtained using the methods. Also provided is a population of iMDSCs. Further provided according to some of the embodiments are iMDSCs expressing PDL1.

Another aspect of the present invention provides a genetically modified myeloid suppressive cell population, genetically modified iMDSC population, subpopulation of genetically modified iMDSCs. In some embodiments, the genetically modified iMDSCs in the above population express or overexpress PDL1.

Further aspect of the present invention provides a modulated population of myeloid suppressive cells, a modulated population of iMDSCs, or a modulated iMDSC subpopulation comprising M-MDSCs, G-MDSCs, or E-MDSCs. A composition comprising such cells, or population or subpopulations thereof is also provided herein.

Yet another aspect of the present invention provides a therapeutic composition comprising the cell, or population or subpopulation thereof, as described herein, and a pharmaceutically acceptable carrier.

One aspect of this invention provides a therapeutic use of the above therapeutic composition by introducing the composition to a subject suitable for adoptive cell therapy, wherein the subject has an autoimmune disorder; a hematological malignancy; a solid tumor; cancer; an infection; a neurodegenerative disease; or an inflammatory condition or disease. Accordingly, the present invention provides a method of treating a subject in need of cell therapy comprising administering a therapeutically sufficient number of cell, or population or subpopulation thereof, as provided herein, to the subject in need. In some embodiments, the subject may be a candidate for bone marrow or stem cell transplantation, or the subject has received chemotherapy or irradiation therapy; or has received bone marrow ablative or non-myeolablative chemotherapy or radiation therapy; or has a hyperproliferative disorder or a cancer of hematopoietic system; or has a solid tumor; or has a virus infection or a disease associated with virus infection; or has an inflammatory condition; or has GvHD. By administering the cells comprising induced myeloid suppressive cells, iMDSCs or subpopulation as provided herein, T cell proliferation and/or effector function are suppressed in vivo, and thus the disease or condition is alleviated.

A further aspect of the present invention provides a method of manufacturing cells for therapeutic use using the compositions and methods as provided in generating iPSC derived cell population comprising induced myeloid suppressive cells, or iMDSC, or M-MDSC, or any subpopulation thereof as disclosed herein.

Various objects and advantages of this use will become apparent from the following description taken in conjunction with the accompanying drawings wherein are set forth, by way of illustration and example, certain embodiments of this invention.

BRIEF DESCRIPTION OF THE DRAWINGS

FIG. 1A: The parental human induced pluripotent stem cells are differentiated through an approximate 10 day multi-staged monolayer culture process to CD34+ hemogenic endothelium. Day 10 iCD34 cells are isolated by FACS and cultured in myeloid promoting conditions resulting CD45+ cells emerging from the endothelial layer starting day 3 after plating and acquiring CD33 by day 9. FIG. 1B: The multistage process produced a population highly enriched for cells with myeloid markers, having CD45+CD33+ cells with a purity more than 95%, and is essentially free of granulocytes, erythrocytes, and lymphoid cells. FIG. 1C: Immunophenotyping by LEGENDScreen™ demonstrates that the day 19 CD45+CD33+ cells express predominantly early myeloid markers. FIG. 1D: The proportion of cell subpopulations in the day 19 MDSCs, including the subpopulation of cells that express immune-regulatory surface proteins including PDL1. FIG. 1E: This process enables the production of over 1,000 CD45+CD33+ cells for 1 iPSC. FIG. 1F: Extending myeloid differentiation to 15 days post seeding of the iCD34 cells increases the percentage of CD45+CD33+ CD14+ iMDSCs.

FIG. 2A: Normalized expansion of T cells from 5 independent donors after co-culture with Day 10+9 iMDSCs; FIG. 2B: Normalized expansion of T cells from 3 independent donors after co-culture with Day 10+15 iMDSCs. FIG. 2C: More significant T cell numbers reduction observed with D10+15 iMDSCs than with D10+9 iMDSCs. All data are presented as averages +/−SEM. **$p<0.0001$, *$p<0.001$, **$p<0.01$, and *$p<0.05$.

FIG. 3A: iMDSCs attenuates the ability of both CD4+ and CD8+ T cells to produce IFNγ, TNF, IL2, and express CD107a. FIG. 3B: T cells cocultured with iMDSCs are less capable of producing multiple effector functions (three or four functions) and are mostly limited to one or two functions. All data are presented as averages +/−SEM. *$p<0.001$, $p<0.01$, and *$p<0.05$.

FIG. 4A: iMDSCs attenuate the severity of disease as measured by GvHD score. FIG. 4B: iMDSCs prolong survival. Kaplan-Meier survival curve was generated using disease endstage (loss of >25% of body weight) as the termination criteria. FIG. 4C: iMDSCs led to a significant reduction in human CD45+ expansion at day 14 with an increase in Tregs (CD4+ CD25$^{hi}$CD127$^{lo}$) in peripheral blood. Data are presented as averages +/−SEM.

DETAILED DESCRIPTION OF THE INVENTION

Figure 1A:
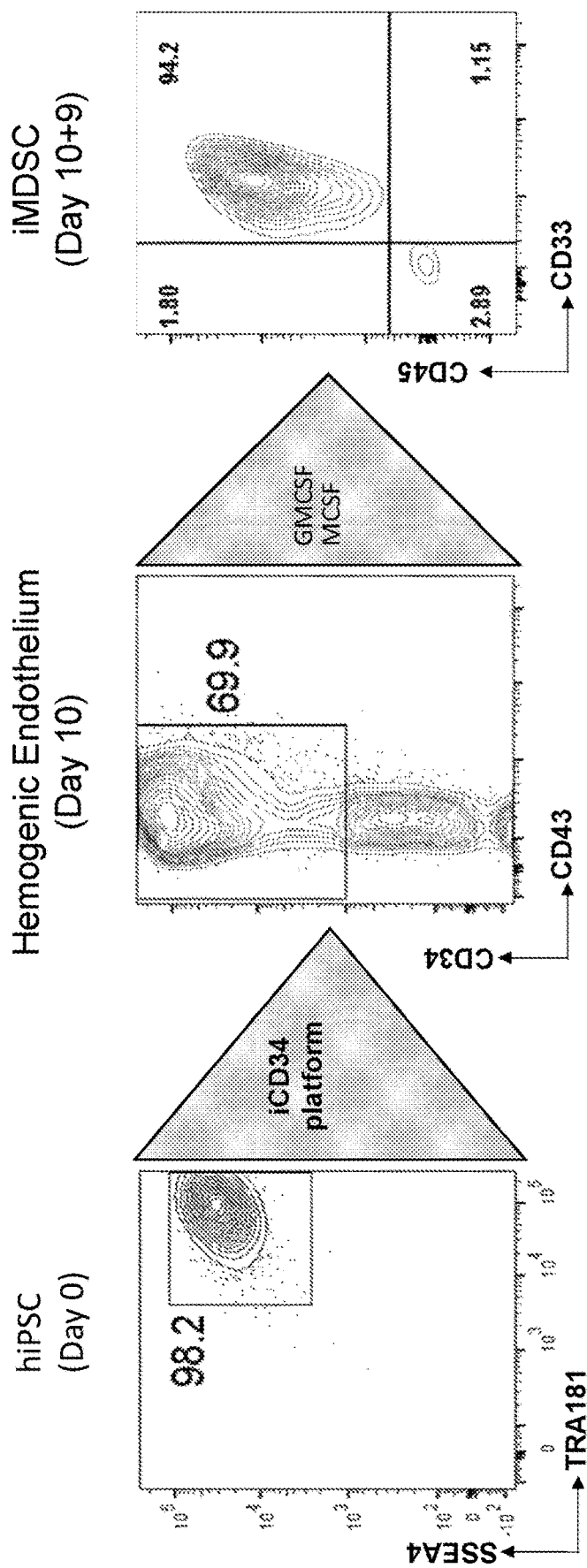
FIGS. 1A-F show the multistage process for generating derived MDSCs from induced pluripotent stem cells (iPSCs) and CD34+ hemogenic endothelium (iHE, iCD34).

The present invention provides compositions and methods of deriving immune regulatory cells from non-pluripotent cells to obtain a population or a subpopulation of induced regulatory cells having desired therapeutic potential for adoptive immunotherapies. The present invention further provides a composition comprising the derived regulatory cells of myeloid lineage having desired therapeutic potential. The present invention also provides methods of using the derived immune regulatory cells including myeloid suppressive cells having desired therapeutic potential for treating diseases and conditions. In general, the derived immune regulatory cells having desired therapeutic potential herein exhibit at least one of the following: increased number or ration of a regulatory cell subtype; and/or improved cell expansion, viability, persistence, homing, and/or inflammatory activating cell suppression. The invention also provides methods of optimizing the derived immune regulatory cell therapeutic potential by genetic modification and small molecule modulation.

A. Definition

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein, the articles "a," "an," and "the" refer to one or to more than one of the grammatical object of the article. By way of example, a T cell means one T cell or more than one T cells.

As used herein, the term "isolated" or the like refers to a cell, or a population of cells, which has been separated from its original environment, i.e., the environment of the isolated cells is substantially free of at least one component as found in the environment in which the "un-isolated" reference cells exist. The term includes a cell that is removed from some or all components as it is found in its natural environment, for example, tissue, biopsy. The term also includes a cell that is removed from at least one, some or all components as the cell is found in non-naturally occurring environments, for example, culture, cell suspension. Therefore, an isolated cell is partly or completely separated from at least one component, including other substances, cells or cell populations, as it is found in nature or as it is grown, stored or subsisted in non-naturally occurring environments. Specific examples of isolated cells include partially pure cells, substantially pure cells and cells cultured in a medium that is non-naturally occurring. Isolated cells may be obtained from separating the desired cells, or populations thereof, from other substances or cells in the environment, or from removing one or more other cell populations or subpopulations from the environment.

As used herein, the term "purify" or the like refers to increasing purity. For example, the purity can be increased to at least 50%, 60%, 70%, 80%, 90%, 95%, 99%, or 100%.

As used herein, the term "immune regulatory cells" refers to various leukocyte sets that have been associated with regulatory functions including, but not limited to, self and non-self discrimination, initiation and modulation of adaptive immune responses, maintenance of self-tolerance, and T cell function suppression. Various immune regulatory cells, include, but are not limited to, myeloid suppressive cells, mesenchymal stromal cells (MSCs), different subsets of T (e.g., Tregs, $T_{FH}$, $T_{FR}$, γδ T cells) and B cells (e.g., Bregs), as well as regulatory innate immune cells (e.g., ILC2).

As used herein, the term "myeloid suppressive cells" refers to regulatory immune cells of myeloid lineage, which include, but are not limited to myeloid-derived suppressor cells (MDSCs), dendritic cells (DCs), and macrophages (Mreg). They are different from other myeloid cell types in which they possess immunosuppressive activities rather than immunostimulatory properties.

As used herein, the term "myeloid-derived suppressor cells" or "MDSCs" refers to a heterogeneous group of immature myeloid cells with immunoregulatory function, characterized by expression of the common myeloid marker CD11b (or CD33), and the absence/low levels of HLADR. As immune regulatory cells, MDSCs possess immunosuppressive activities rather than immunostimulatory properties. In steady-state conditions, MDSC precursors reside primarily in the bone marrow. In healthy individuals, MDSC precursors formed in the bone marrow differentiate to dendritic cells, macrophages and neutrophils. However, in different pathological conditions such as malignant tumors, infections, inflammation, transplanted organs and autoimmune diseases, myeloid differentiation is skewed towards the expansion of MDSCs, and they can be detected in the blood, peripheral lymphoid tissues, the spleen, cancerous tissues and inflammatory sites including different grafted organs. These MDSCs infiltrate inflammation sites and tumors, where they stop immune responses by inhibiting T cells and NK cells. MDSCs also interact with other immune regulatory cell types including dendritic cells and macrophages to regulate their functions and immune responses. As disclosed herein, the induced MDSCs, derived from iPSC or iCD34, comprise one or more of the subtypes: (i) $CD45^+$ cells; (ii) $CD45^+CD33^+$ cells; (iii) monocytic MDSCs (M-MDSCs); (iv) $CD45^+CD33^+CD14^+$ cells; (v) granulocytic MDSCs (G-MDSCs); and (vi) $CD45^+CD14^-CD15^+CD11b^+$.

As used herein, the term "monocytic MDSC" or "M-MDSC" refers to cells characterized by, for example, $CD45^+$, $CD33^+$, $CD14^+$. Monocytic MDSCs may further comprises one or more of $CD11b^+$, $CD66^-$(or $CD15^-$), and $HLADR^{low}$.

As used herein, the term "granulocytic MDSC" or "G-MDSC" refers to cells characterized by, for example, $CD11b^+$, $CD14^-$, $CD15^+$, $CD33^{dim}$.

As used herein, the term "dendritic cell" refers to cells comprising $CD45^+$, $CD11c^+$, $CD14-$, and $HLADR^{high}$.

As used herein, the term "macrophage" refers to cells comprising $CD45^+$ and $CD206^+$. In some subpopulation, the macrophage also expresses one or more of CD11b, CD86, CD163 and CD68. Regulatory macrophages produce high levels of anti-inflammatory cytoknines such as IL10 compared to immune stimulatory macrophages which produce pro-inflammatory cytokines IL12. A regulatory macrophage can be repolarized to a stimulatory macrophage under heavy pro-inflammatory conditions.

As used herein, the term "population" when used with reference to immune cells refers to a group of one or more immune cell types or subtypes thereof including, but not limited to, macrophages, dendritic cells, myeloid-derived suppressor cells (MDSCs), monocytes, megakaryocytes, neutrophils, eosinophils, T, B, NK, and NKT cells. Using MDSCs as an example, the isolated, or enriched, population of MDSCs may include only one subtype of MDSCs, or may include a mixture of two or more subtypes of MDSCs. The isolated population of MDSCs can be a homogeneous population of one subtype of MDSCs or a heterogeneous population of two or more subtypes of MDSCs. The isolated population of MDSCs can also be a heterogeneous population having MDSCs and at least a cell type other than a MDSC, e.g., a B cell, a T cell, a macrophage, a neutrophil, an erythrocyte, a hepatocyte, an endothelial cell, an epithelial cell, a muscle cell, a brain cell, etc. The heterogeneous population can have from 0.01% to about 100% MDSCs. Accordingly, an isolated population of MDSCs can have at least 50%, 60%, 70%, 80%, 90%, 95%, 98%, or 99% MDSCs. The isolated population of MDSCs can include one or more, or all of, the different subtypes of MDSCs, including but not limited to monocytic-MDSCs, granulocytic-MDSCs, early-stage MDSCs (eMDSCs; characterized by, for example, $CD33^+$, $Lin^-$, $HLADR^-$). In an isolated population of MDSCs that includes more than one subtype of MDSCs, the relative ratio of each subtype of MDSCs can range from 0.01% to 99.99%. The isolated population also can be a clonal population of an MDSC, in which all the MDSCs of the population are clones of a single MDSC. In some embodiment, An isolated population of immune cell may be obtained from a natural source, such as human peripheral blood or cord blood, or from an in vitro setting, such as the immune regulatory cells differentiated from iPSCs or induced definitive hemogenic endothelium cells, as provided herein. Various ways of dissociating cells from tissues or cell mixtures to separate the various cell types have been developed in the art. In some cases, these manipulations result in a relatively homogeneous population of cells. For example, the induced MDSCs, induced macrophages, or induced dendritic cells, or any subpopulation thereof, can be isolated by a sorting or selection process as described herein or by other methods known in the art. The proportion of iMDSCs in the isolated population may be higher than the proportion of MDSCs in the natural source by at least about 10%, about 20%, about 30%, about 40%, about 50%, about 60%, about 70%, about 80%, about 85%, about 90%, or about 95%. The isolated population of iMDSCs can be for iMDSCs in general, or one or more specific subtypes of iMDSCs such as M-MDSCs, G-MDSCs.

As used herein, the term "subpopulation" when used in reference to MDSCs, refers to a population of MDSCs that includes one or more subtypes but less than all subtypes of MDSCs that are found in nature. For example, MDSCs comprises at least monocytic-, granulocytic-, early-stage-MDSC subtypes, each of which may be further divided into more subtypes based on surface markers and/or functions.

As used herein, the term "pluripotent" refers to the ability of a cell to form all lineages of the body or soma (i.e., the embryo proper). For example, embryonic stem cells are a type of pluripotent stem cells that are able to form cells from each of the three germs layers, the ectoderm, the mesoderm, and the endoderm. Pluripotency is a continuum of developmental potencies ranging from the incompletely or partially pluripotent cell (e.g., an epiblast stem cell or EpiSC), which is unable to give rise to a complete organism to the more primitive, more pluripotent cell, which is able to give rise to a complete organism (e.g., an embryonic stem cell).

As used herein, the term "induced pluripotent stem cells" or, "iPSCs," refers to stem cells produced from differentiated adult cells that have been induced or changed (i.e. reprogrammed) into cells capable of differentiating into tissues of all three germ or dermal layers: mesoderm, endoderm, and ectoderm.

As used herein, the term "embryonic stem cell" refers to naturally occurring pluripotent stem cells of the inner cell mass of the embryonic blastocyst. Embryonic stem cells are pluripotent and give rise during development to all derivatives of the three primary germ layers: ectoderm, endoderm and mesoderm. They do not contribute to the extra-embryonic membranes or the placenta and are not totipotent.

As used herein, the term "progenitor cell" refers to cells that have greater developmental potential, i.e., a cellular phenotype that is more primitive (e.g., is at an earlier step along a developmental pathway or progression) relative to a cell which it can give rise to by differentiation. Often, progenitor cells have significant or very high proliferative potential. Progenitor cells can give rise to multiple distinct cells having lower developmental potential, i.e., differentiated cell types, or to a single differentiated cell type, depending on the developmental pathway and on the environment in which the cells develop and differentiate.

As used herein, the terms "reprogramming" or "dedifferentiation" or "increasing cell potency" or "increasing developmental potency" refers to a method of increasing the potency of a cell or dedifferentiating the cell to a less differentiated state. For example, a cell that has an increased cell potency has more developmental plasticity (i.e., can differentiate into more cell types) compared to the same cell in the non-reprogrammed state. In other words, a reprogrammed cell is one that is in a less differentiated state than the same cell in a non-reprogrammed state.

As used herein, the term "differentiation" is the process by which an unspecialized ("uncommitted") or less specialized cell acquires the features of a specialized cell such as, for example, a blood cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type.

As used herein, the term "multipotent stem cell" refers to a cell that has the developmental potential to differentiate into cells of one or more germ layers (ectoderm, mesoderm and endoderm), but not all three. Thus, a multipotent cell can also be termed a "partially differentiated cell." Multipotent cells are well known in the art, and examples of multipotent cells include adult stem cells, such as for example, hematopoietic stem cells and neural stem cells. "Multipotent" indicates that a cell may form many types of cells in a given lineage, but not cells of other lineages. For example, a multipotent hematopoietic cell can form the many different types of blood cells (red, white, platelets, etc.), but it cannot form neurons. Accordingly, the term "multipotency" refers to a state of a cell with a degree of developmental potential that is less than totipotent and pluripotent.

Differentiation of pluripotent stem cells requires a change in the culture system, such as changing the stimuli agents in the culture medium or the physical state of the cells. The most conventional strategy utilizes the formation of embryoid bodies (EBs) as a common and critical intermediate to initiate the lineage-specific differentiation. EBs are three-dimensional clusters that have been shown to mimic embryo development as they give rise to numerous lineages within their three-dimensional area. Through the differentiation process, typically few hours to days, simple EBs (for example, aggregated pluripotent stem cells elicited to differentiate) continue maturation and develop into a cystic EB at which time, typically days to few weeks, they are further processed to continue differentiation. EB formation is initiated by bringing pluripotent stem cells into close proximity with one another in three-dimensional multilayered clusters of cells, typically this is achieved by one of several methods including allowing pluripotent cells to sediment in liquid droplets, sedimenting cells into "U" bottomed well-plates or by mechanical agitation. To promote EB development, the pluripotent stem cell aggregates require further differentiation cues, as aggregates maintained in pluripotent culture maintenance medium do not form proper EBs. As such, the pluripotent stem cell aggregates need to be transferred to differentiation medium that provides eliciting cues towards the lineage of choice. EB-based culture of pluripotent stem cells typically results in generation of differentiated cell populations (ectoderm, mesoderm and endoderm germ layers) with modest proliferation within the EB cell cluster. Although proven to facilitate cell differentiation, EBs, however, give rise to heterogenous cells in variable differentiation state because of the inconsistent exposure of the cells in the three-dimensional structure to differentiation cues from the environment. In addition, EBs are laborious to create and maintain. Moreover, cell differentiation through EB is accompanied with modest cell expansion, which also contributes to low differentiation efficiency.

In comparison, "aggregate formation," as distinct from "EB formation," can be used to induce differentiation of pluripotent stem cells and/or to expand the populations of pluripotent stem cell derived cells. For example, during aggregate-based pluripotent stem cell expansion, culture media are selected to maintain proliferation and pluripotency. Cells proliferation generally increases the size of the aggregates forming larger aggregates, these aggregates can be routinely mechanically or enzymatically dissociated into smaller aggregates to maintain cell proliferation within the culture and increase numbers of cells. As distinct from EB culture, cells cultured within aggregates in maintenance culture maintain markers of pluripotency.

As used herein, "monolayer differentiation" is a term referring to a differentiation method distinct from differentiation through three-dimensional multilayered clusters of cells, i.e., "EB formation." Monolayer differentiation, among other advantages disclosed herein, avoids the need for EB formation for differentiation initiation. Because monolayer culturing does not mimic embryo development such as EB formation, differentiation towards specific lineages are minimal as compared to all three germ layer differentiation in EB.

As used herein, a "dissociated" cell refers to a cell that has been substantially separated or purified away from other cells or from a surface (e.g., a culture plate surface). For example, cells can be dissociated from an animal or tissue by mechanical or enzymatic methods. Alternatively, cells that aggregate in vitro can be dissociated from each other, such as by dissociation into a suspension of clusters, single cells or a mixture of single cells and clusters, enzymatically or mechanically. In yet another alternative embodiment, adherent cells are dissociated from a culture plate or other surface. Dissociation thus can involve breaking cell interactions with extracellular matrix (ECM) and substrates (e.g., culture surfaces), or breaking the ECM between cells.

As used herein, the term "encoding" refers to the inherent property of specific sequences of nucleotides in a polynucleotide, such as a gene, a cDNA, or a mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "exogenous" is intended to mean that the referenced molecule or the referenced activity is introduced into the host cell. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the cell. The term "endogenous" refers to a referenced molecule or activity that is present in the host cell. Similarly, the term when used in reference to expression of an encoding nucleic acid refers to expression of an encoding nucleic acid contained within the cell and not exogenously introduced.

As used herein, the term "polynucleotide" refers to a polymeric form of nucleotides of any length, either deoxyribonucleotides or ribonucleotides or analogs thereof. The sequence of a polynucleotide is composed of four nucleotide bases: adenine (A); cytosine (C); guanine (G); thymine (T); and uracil (U) for thymine when the polynucleotide is RNA. A polynucleotide can include a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. Polynucleotide also refers to both double- and single-stranded molecules.

As used herein, the term "peptide," "polypeptide," and "protein" are used interchangeably and refer to a molecule having amino acid residues covalently linked by peptide bonds. A polypeptide must contain at least two amino acids, and no limitation is placed on the maximum number of amino acids of a polypeptide. As used herein, the terms refer to both short chains, which are also commonly referred to in the art as peptides, oligopeptides and oligomers, for example, and to longer chains, which generally are referred to in the art as polypeptides or proteins. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural polypeptides, recombinant polypeptides, synthetic polypeptides, or a combination thereof.

As used herein, the term "ex vivo" refers to activities that take place outside an organism, such as experimentation or measurements done in or on living tissue in an artificial environment outside the organism, preferably with minimum alteration of the natural conditions. The "ex vivo" procedures can involve living cells or tissues taken from an organism and cultured in a laboratory apparatus, usually under sterile conditions, and typically for a few hours or up to about 24 hours, but including up to 2 to 28 days, depending on the circumstances. Such tissues or cells can also be collected and frozen, and later thawed for ex vivo treatment. Tissue culture experiments or procedures lasting longer than a few days using living cells or tissue are typically considered to be "in vitro," though in certain embodiments, this term can be used interchangeably with ex vivo. Meanwhile, an "in vivo" activity takes place in an organism, for example, a mouse, wherein such activities may include cell engraftment, cell homing, self-renewal of cells, and expansion of cells.

As used herein, the term "in vitro" refers to activities performed or taking place in a test tube, culture dish, or elsewhere outside of a living organism.

As used herein, the terms "contact," "treat," or "modulate," when used in reference to an immune cell, are used interchangeably herein to refer to culturing, incubating or exposing an immune cell with one or more of the agents disclosed herein.

As used herein, a "noncontacted" or an "untreated" cell is a cell that has not been treated, e.g., cultured, contacted, or incubated with an agent other than a control or vehicle agent. Cells contacted with a control agent, such as DMSO, or contacted with another vehicle are examples of noncontacted cells.

As used herein, "feeder cells" or "feeders" are terms describing cells of one type that are co-cultured with cells of a second type to provide an environment in which the cells of the second type can grow, expand, or differentiate, as the feeder cells provide stimulation, growth factors and nutrients for the support of the second cell type. The feeder cells are optionally from a different species as the cells they are supporting. For example, certain types of human cells, including stem cells, can be supported by primary cultures of mouse embryonic fibroblasts, or immortalized mouse embryonic fibroblasts. In another example, peripheral blood derived cells or transformed leukemia cells support the expansion and maturation of natural killer cells. The feeder cells may typically be inactivated when being co-cultured with other cells by irradiation or treatment with an anti-mitotic agent such as mitomycin to prevent them from outgrowing the cells they are supporting. Feeder cells may include endothelial cells, stromal cells (for example, epithelial cells or fibroblasts), and leukemic cells. Without limiting the foregoing, one specific feeder cell type may be a human feeder, such as a human skin fibroblast. Another feeder cell type may be mouse embryonic fibroblasts (MEF). In general, various feeder cells can be used in part to maintain pluripotency, direct differentiation towards a certain lineage, enhance proliferation capacity and promote maturation to a specialized cell types, such as an effector cell.

As used herein, a "feeder-free" (FF) environment refers to an environment such as a culture condition, cell culture or culture media which is essentially free of feeder or stromal cells, and/or which has not been pre-conditioned by the cultivation of feeder cells. "Pre-conditioned" medium refers to a medium harvested after feeder cells have been cultivated within the medium for a period of time, such as for at least one day. Pre-conditioned medium contains many mediator substances, including growth factors and cytokines secreted by the feeder cells cultivated in the medium. In some embodiments, a feeder-free environment is free of both feeder or stromal cells and is also not pre-conditioned by the cultivation of feeder cells.

As used herein, the term "analogue" refers to a chemical molecule that is similar to another chemical substance in structure and function, differing structurally by one single element or group, or more than one group (e.g., 2, 3, or 4 groups) if it retains the same chemical scaffold and function as the parental chemical. Such modifications are routine to persons skilled in the art, and include, for example, additional or substituted chemical moieties, such as esters or amides of an acid, protecting groups such as a benzyl group for an alcohol or thiol, and tert-butoxylcarbonyl groups for an amine. Also included are modifications to alkyl side chains, such as alkyl substitutions (e.g., methyl, dimethyl, ethyl, etc.), halogen addition, modifications to the level of saturation or unsaturation of side chains, and the addition of modified groups such as substituted phenyl and phenoxy. Analogues can also include conjugates, such as biotin or avidin moieties, enzymes such as horseradish peroxidase and the like, and including radio-labeled, bioluminescent, chemoluminescent, or fluorescent moieties. Also, moieties can be added to the agents described herein to alter their pharmacokinetic properties, such as to increase half-life in vivo or ex vivo, or to increase their cell penetration properties, among other desirable properties. Also included are prodrugs, which are known to enhance numerous desirable qualities of pharmaceuticals (e.g., solubility, bioavailability, manufacturing, etc.).

As used herein, the term "increase" refers to the ability of an agent to produce or cause a greater physiological response (i.e., downstream effects) in a cell, as compared to the response caused by either vehicle or a control molecule/composition, e.g., increased production of interleukin 2 or TNF by an isolated population of T cells. The increase can be an increase in gene expression as a result of increased signaling through certain cell signaling pathways. An "increased" amount is typically a statistically significant amount, and can include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) compared to the response produced by vehicle (the absence of an agent) or a control composition.

As used herein, the term "decrease" refers to the ability of an agent to produce or cause a lesser physiological response (i.e., downstream effects) in a cell, as compared to the response caused by either vehicle or a control molecule/composition. The decrease can be a decrease in gene expression, a decrease in cell signaling, or a decrease in cell proliferation. A "decreased" amount is typically a "statistically significant" amount, and can include a decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle (the absence of an agent) or a control composition.

As used herein, the term "synergy" or "synergistic" refers to a combination of two or more entities for an enhanced effect such that the working together of the two or more entities produces an effect greater than the sum of their individual effects, as compared to "antagonistic," which is used when two or more entities in a combination counteract or neutralize each other's effect; and compared to "additive," which is used when two or more entities in a combination produce an effect nearly equal to the sum of their individual effects.

As used herein, the terms "substantially free of," when used to describe a composition, such as a cell population or culture media, refers to a composition that is free of a specified substance of any source, such as, 95% free, 96% free, 97% free, 98% free, 99% free of the specified substance, or is undetectable as measured by conventional means. Similar meaning can be applied to the term "absence of," where referring to the absence of a particular substance or component of a composition.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. The range of quantity, level, value, number, frequency, percentage, dimension, size, amount, weight or length can be ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

As used herein, the term "subject," refers to a mammal. A subject can be a human or a non-human mammal such as a dog, cat, bovid, equine, mouse, rat, rabbit, or transgenic species thereof.

As used herein, the terms "treat," "treatment" and the like, when used in reference to a subject in need of a therapeutic treatment, refer to obtaining a desired pharmacologic and/or physiologic effect, including without limitation achieving an improvement or elimination of the symptoms of a disease. The effect can be prophylactic in terms of completely or partially preventing a disease or symptom thereof and/or can be therapeutic in terms of achieving an improvement or elimination of symptoms, or providing a partial or complete cure for a disease and/or adverse effect attributable to the disease. The term "treatment" includes any treatment of a disease in a mammal, particularly in a human, and includes: (a) preventing the disease from occurring in a subject which can be predisposed to the disease but has not yet been diagnosed as having it; (b) inhibiting the disease, or arresting its development; (c) relieving the disease, or causing regression of the disease, or completely or partially eliminating symptoms of the disease; and (d) restoring the individual to a pre-disease state, such as reconstituting the hematopoietic system.

As used herein, "genetic modification" refers to genetic alteration including those (1) naturally derived from rearrangements, mutations, genetic imprinting and/or epigenetic modification, or (2) obtained through genomic engineering through insertion, deletion or substitution in the genome of a cell, whether it is locus specific or locus non-specific. Genetic modification, as used herein, also includes one or more retainable therapeutic attributes of a source-specific immune cell that is donor-, disease-, or treatment response-specific.

As used herein, the term "genetic imprint" refers to genetic or epigenetic information that contributes to preferential therapeutic attributes in a source cell. In the aspect of a source cell obtained from a specifically selected donor, disease or treatment context, the genetic imprint contributing to preferential therapeutic attributes may include any context-specific genetic or epigenetic modifications which manifest a retainable phenotype, i.e. a preferential therapeutic attribute, irrespective of the underlying molecular events being identified or not. Donor-, disease-, or treatment response-specific source cells may comprise genetic imprints that are retainable in iPSCs and derived hematopoietic lineage cells. These genetic imprints include but are not limited to, a monospecific TCR, for example, from a viral specific T cell or invariant natural killer T (iNKT) cell; trackable and desirable genetic polymorphisms, for example, homozygous for a point mutation that encodes for the high-affinity CD16 receptor in selected donors; and predetermined HLA requirements, i.e., selected HLA-matched donor cells exhibiting a common haplotype. As used herein, preferential therapeutic attributes include improved engraftment, trafficking, homing, viability, self-renewal, persistence, immune response regulation and modulation, survival, and cytotoxicity of a derived cell. A preferential therapeutic attribute may also relate to antigen targeting receptor expression; HLA presentation or lack thereof; resistance to the immunosuppressive effects of the tumor microenvironment; induction of bystander immune cells and desirable immune modulation; improved on-target specificity with reduced off-tumor effect; and resistance to treatment such as chemotherapy.

As used herein, the term "safety switch protein" refers to an engineered protein designed to prevent potential toxicity or otherwise adverse effects of a cell therapy. In some instances, the safety switch protein expression is conditionally controlled to address safety concerns for transplanted engineered cells that have permanently incorporated the gene encoding the safety switch protein into its genome. This conditional regulation could be variable and might include control through a small molecule-mediated post-translational activation and tissue-specific and/or temporal transcriptional regulation. The safety switch could mediate induction of apoptosis, inhibition of protein synthesis or DNA replication, growth arrest, transcriptional and post-transcriptional genetic regulation and/or antibody-mediated depletion. In some instance, the safety switch protein is activated by an exogenous molecule, e.g. a prodrug, that, when activated, triggers apoptosis and/or cell death of a therapeutic cell. Examples of safety switch proteins, include, but are not limited to suicide genes such as caspase 9 (or caspase 3 or 7), thymidine kinase, cytosine deaminase, B-cell CD20, modified EGFR, and any combination thereof. In this strategy, a prodrug that is administered in the event of an adverse event is activated by the suicide-gene product and kills the transduced cell.

A "therapeutically sufficient amount", as used herein, includes within its meaning a non-toxic but sufficient and/or effective amount of the particular therapeutic and/or pharmaceutical composition to which it is referring to provide a desired therapeutic effect. The exact amount required will vary from subject to subject depending on factors such as the patient's general health, the patient's age and the stage and severity of the condition. In particular embodiments, a therapeutically sufficient amount is sufficient and/or effective to ameliorate, reduce, and/or improve at least one symptom associated with a disease or condition of the subject being treated.

B. Overview

The invention generally relates to a multistage process of differentiating a pluripotent cell to non-pluripotent cells or partially differentiated cells, including, mesodermal cells, hemogenic endothelium, hematopoietic stem or progenitor cells, $CD34^+$ cells, multipotent progenitors (MPP) (capable of differentiating into myeloid, including neutrophil progenitors), and myeloid-derived suppressor cells (MDSCs). The invention also relates to the compositions used in the disclosed methods; and cell populations, cell lines, or clonal cells generated using the disclosed methods.

The present invention also provides a manufacturing process to generate MDSCs (iMDSCs) induced or derived from human induced pluripotent stem cells (iPSCs). The process is GMP-compatible, serum/feeder-free, and is highly scalable and efficient. The generated iMDSC population is highly homogeneous, i.e., essentially free of erythrocytes and lymphoid cells; and highly functional including in suppressing T cell effector function independently of HLA matching and attenuating Graft-versus-Host-Disease (GvHD). As such, the iMDSCs and cell population of this invention can serve as a scalable, "off-the-shelf" source of immunoregulatory cells for the treatment of autoimmune and inflammatory diseases.

I. Composition and Methods for Generating Pluripotent Stem Cell Derived Immuno-Regulatory Cells One aspect of the present invention provides a culture platform for obtaining induced immuno-regulatory cells, including, but not limited to myeloid-derived suppressor cells (MDSCs), regulatory T cells, regulatory B cells, macrophages, dendritic cells, and mesenchymal stromal cells, by differentiating pluripotent cells or multipotent progenitor cells. Another aspect of the present invention provides a method for producing pluripotent cell or multipotent progenitor cell derived immuno-regulatory cells comprising at least MDSCs. In one particular embodiment, the present invention provides compositions and methods for obtaining induced MDSCs by differentiating pluripotent cells or multipotent progenitor cells. As used herein, pluripotent cell or multipotent progenitor cell derived MDSCs are collectively termed iMDSCs, or induced MDSCs. As used herein, pluripotent cells include, but are not limited to, pluripotent stem cells, induced pluripotent stem cells (iPSCs), and multipotent progenitor cells. In some embodiment, pluripotent stem cells are embryonic stem cells. In some embodiment, multipotent progenitor cells are hemogenic endothelium cells. In some embodiment, the hemogenic endothelium cells express CD34 (iCD34, also called definitive HE or iHE).

One aspect of the invention provides a method of using an optimized multistage process to generate definitive hemogenic endothelium (iHE), which can be then used to differentiate and obtain iMDSCs. Generally, the method begins with a first stage wherein pluripotent stem cells are seeded and expanded. The pluripotent stem cells are then differentiated to mesodermal cells, which expand in this stage. The expanded mesodermal population is then differentiated to a mesodermal population with definitive hemogenic endothelium potential, definitive hemogenic endothelium are then differentiated and expanded from the mesodermal cells with definitive hemogenic endothelium potential. Alternatively, the invention provides a method of generating definitive hemogenic endothelium (iHE) that comprises differentiating and expanding mesodermal cells from pluripotent stem cells; then definitive hemogenic endothelium (iHE) are differentiated and expanded from mesodermal cells. In some embodiments, the pluripotent stem cells are iPSCs. In some embodiments, the iPSCs are naïve iPSCs. The invention further provides a method of generating and expanding definitive hemogenic endothelium (iHE) that comprises differentiating and expanding pluripotent stem cell-derived mesodermal cells, and obtaining mesodermal cells having definitive iHE potential, which are then differentiated into iHE. Alternatively, the invention provides a method of generating and expanding definitive hemogenic endothelium comprises differentiating pluripotent stem cell-derived mesodermal cells to iHE. The methods disclosed herein utilize the optimized monolayer iCD34 culture platform without EB formation, and optionally, is free, or essentially free, of TGFβ receptor/ALK inhibitors.

In one embodiment, the culture platform for obtaining iHE using pluripotent stem cells including iPSCs comprises a seeding medium comprising MEKi, GSKi, and ROCKi. In some embodiments, the seeding medium is free of, or essentially free of, TGFβ receptor/ALK inhibitors. In one embodiment, the combinations of the small molecules in the seeding culture media of the invention are shown in Table 1 as Fate Maintenance Medium (FMM). The components of the medium may be present in the medium in amounts within the concentration ranges shown in Table 1. In one embodiment, the iPSC used for obtaining definitive hemogenic endothelium was a cell line generated using the Fate Reprogramming Medium (FRM), and further maintained in FMM to establish and sustain the ground or naïve state of the iPSC cell line, which is suitable for stage specific differentiation as disclosed herein. The ground or naïve iPSC so obtained is amenable to cryopreservation. In the present invention, an iPSC cell line or a clonal iPSC preserved may be seeded in FMM for the subsequence differentiation into definitive hemogenic endothelium.

TABLE 1

Seeding culture for Naïve iPSC to obtain CD34+ hemogenic endothelium:

| Conventional hESC Medium (Conv.) | Fate Reprogramming Medium (FRM) | Fate Maintenance Medium (FMM) |
|---|---|---|
| DMEM/F12 | DMEM/F12 | DMEM/F12 |
| Knockout Serum Replacement (20%) | Knockout Serum Replacement (20%) | Knockout Serum Replacement (20%) |
| | N2 | |
| | B27 | |

TABLE 1-continued

Seeding culture for Naïve iPSC to obtain CD34+ hemogenic endothelium:

| Conventional hESC Medium (Conv.) | Fate Reprogramming Medium (FRM) | Fate Maintenance Medium (FMM) |
|---|---|---|
| Glutamine | Glutamine | Glutamine (1x) |
| Non-Essential Amino Acids (1x) | Non-Essential Amino Acids (1x) | Non-Essential Amino Acids (1x) |
| β-mercaptoethanol (100 μM) | β-mercaptoethanol (100 μM) | β-mercaptoethanol (100 μM) |
| bFGF (0.2-50 ng/mL) | bFGF (2-500 ng/mL) | bFGF (2-500 ng/mL) |
| | LIF (0.2-50 ng/mL) | LIF (0.2-50 ng/mL) |
| | Thiazovivin (0.1-25 μM) | Thiazovivin (0.1-25 μM) |
| | PD0325901 (0.005-2 μM) | PD0325901 (0.005-2 μM) |
| | CHIR99021 (0.02-5 μM) | CHIR99021 (0.02-5 μM) |
| | SB431542 (0.04-10 μM) | |
| In combination with MEF feeder cells | Feeder-free, in combination with Matrigel™ or Vitronectin | |

One aspect of the present invention provides a culture medium for mesoderm differentiation and expansion from pluripotent stem cells including iPSCs. In some embodiments, the iPSC is naïve iPSC. In one embodiment, the culture medium comprises a BMP activator, and optionally a bFGF, and a CD34 base medium comprising small molecules in a combination as shown in Table 2. In some embodiments, the culture medium comprises an extracellular matrix protein. In other embodiments, the culture medium herein comprises one or more of small molecules, growth factors, and/or cytokines in concentration ranges as shown in Table 2. In some embodiments, the culture medium is fully defined with the substitution of Matrigel™ for Vitronectin.

TABLE 2

| iCD34-A culture medium for obtaining mesoderm from iPSC | |
|---|---|
| base medium | StemPro 34 |
| | Glutamine |
| | Non-Essential Amino Acids |
| | Ascorbic Acid (1-250 ng/ml) |
| | MTG (10-2500 μM) |
| BMP4 (0.05-15 ng/ml) | |
| Feeder-free, in combination with Matrigel™ or Vitronectin | |

In one embodiment, the above culture medium for mesoderm differentiation and expansion from pluripotent stem cells further comprises bFGF between 0.2-50 ng.

One aspect of the present invention provides a culture medium for obtaining mesodermal cells with definitive hemogenic endothelium potential from pluripotent stem cells including iPSCs. In some embodiments, the iPSC is naïve iPSC. In one embodiment, the culture medium comprises a BMP activator, a GSK3 inhibitor and bFGF. In one embodiment, the culture medium comprising GSK3 inhibitor is only applied after mesodermal cell specification in order to achieve definitive HE potential. In one embodiment the culture medium comprising a BMP activator, a GSK3 inhibitor and bFGF, further comprises a CD34 base medium comprising small molecules in a combination as shown in Table 3. In one embodiment, the above culture medium is free of TGFβ receptor/ALK inhibitors. In some embodiments, the culture medium comprises an extracellular matrix protein. In other embodiments, the culture medium herein comprises small molecules, growth factors, and/or cytokines in concentration ranges as shown in Table 3. In some embodiments, the culture medium is fully defined with the substitution of Matrigel™ for Vitronectin.

TABLE 3 iCD34-B culture medium for obtaining mesodermal cells with definitive hemogenic endothelium potential

| base medium | StemPro 34 |
| --- | --- |
| | Glutamine |
| | Non-Essential Amino Acids |
| | Ascorbic Acid (1-250 ng/ml) |
| | MTG (10-2500 µM) |
| BMP4 (0.05-15 ng/ml) | |
| bFGF (0.2-50 ng/ml) | |
| CHIR99012 (0.04-10 µM) | |
| Feeder-free, in combination with Matrigel ™ or Vitronectin | |

One aspect of the present invention provides a culture medium for obtaining definitive hemogenic endothelium (iHE, or iCD34+) from mesodermal cells. In one embodiment, the culture medium comprises a ROCK inhibitor, and one or more growth factors and cytokines selected from the group consisting of VEGF, bFGF, SCF, IL6, and IL11. In one embodiment, the culture medium comprises VEGF, bFGF, SCF, IL6, IL11 and a ROCK inhibitor, and a CD34 base medium comprising small molecules in a combination as shown in Table 4. In one embodiment the culture medium comprising VEGF, bFGF, SCF, IL6, IL11 and a ROCK inhibitor is free of IGF1 and/or EPO. In other embodiments, the culture medium herein comprises small molecules, growth factors, and/or cytokines in concentration ranges as shown in Table 4.

TABLE 4 iCD34-C culture medium for obtaining definitive hemogenic endothelium from mesoderm having hemogenic endothelium potential

| base medium | StemPro 34 |
| --- | --- |
| | Glutamine |
| | Non-Essential Amino Acids |
| | Ascorbic Acid (1-250 ng/ml) |
| | MTG (10-2500 µM) |
| VEGF (0.2-50 ng/ml) | |
| bFGF (0.1-25 ng/ml) | |
| SCF (1-250 ng/ml) | |
| IL6 (0.2-50 ng/ml) | |
| IL11 (0.2-50 ng/ml) | |
| Y27632 (0.2-50 µM) | |
| Feeder-free, in combination with Matrigel ™ or Vitronectin | |

One aspect of the present invention provides a culture platform for obtaining myeloid suppressive cells including myeloid-derived suppressor cells (MDSC) from THE (iCD34). In one embodiment, the culture platform comprises (i) a culture medium comprising a ROCK inhibitor and MCSF, and one or more growth factors and cytokines selected from the group consisting of IL1b, IL3, IL6, IL4, IL10, IL13, TGFβ, bFGF, VEGF, SCF, GMCSF, and FLT3L, and optionally, one or both of an AhR (aryl hydrocarbon receptor) antagonist and a prostaglandin pathway agonist, wherein the culture medium is suitable for differentiating definitive hemogenic endothelium into a MDSC (iMDSC) (Table 5). In some embodiments, IL3 is included in the medium for iMDSC differentiation. In some embodiments, IL4 and GMCSF are included in the medium to induce dendritic cells. In some other embodiments, IL3, IL4 and IL10 are included in the medium to induce macrophages. In some embodiments, the ROCK inhibitor is thiazovivin or Y27632. In some embodiments, the ROCK inhibitor is Y27632. In some embodiments, the AhR antagonist is StemRegenin1 (SR1). In some other embodiments, the prostaglandin pathway agonist is PGE2, or derivatives and analogs thereof. As used herein, "analogues or derivatives" include, but are not limited to, salt, ester, ether, solvate, hydrate, stereoisomer or prodrug of a compound. In other embodiments, the culture medium herein comprises small molecules, growth factors, and/or cytokines in concentration ranges as exemplified in Table 5.

TABLE 5

MDSC culture medium for obtaining myeloid suppressive cell from iCD34

| base medium | StemPro 34 |
| --- | --- |
| | Glutamine |
| | Non-Essential Amino Acids |
| | Ascorbic Acid (1-250 ng/ml) |
| | MTG (10-2500 µM) |
| VEGF (0.2-50 ng/ml) | |
| bFGF (0.2-25 ng/ml) | |
| SCF (1-250 ng/ml) | |
| MCSF (1-250 ng/ml) | |
| GMCSF (2-500 ng/ml) | |
| IL3 (0.5-150 ng/ml) | |
| FLT3L (0.5-150 ng/ml) | |
| Y27632 (0.2-50 µM)* | *not included when differentiating the pre-HSC into multipotent progenitors |
| StemRegenin1 (500-1000 nM) | |
| Feeder-free, in combination with Matrigel ™ or Vitronectin | |

In one embodiment of the method of producing myeloid suppressive cells including iMDSCs from definitive HE, and the method comprises contacting the definitive HE with a medium comprising a ROCK inhibitor and MCSF, and one or more growth factors and cytokines selected from the group consisting of IL1b, IL3, IL6, IL4, IL10, IL13, TGFβ, bFGF, VEGF, SCF, GMCSF, and FLT3L, and optionally, one or both of an AhR antagonist and a prostaglandin pathway agonist. In one embodiment, the medium composition for generating a population of iMDSCs comprises a ROCK inhibitor, MCSF, IL3, VEGF, bFGF, SCF, and FLT3L. In some embodiments, said medium comprising a ROCK inhibitor, MCSF, IL3, VEGF, bFGF, SCF, and FLT3L further comprises one or more of IL1b, IL6, IL10, and TGFβ. In some embodiments, the medium composition does not include IL6. In some embodiments, the medium composition does not require TPO. In some embodiments, the medium composition further comprises feeder cell or feeder cell components. In some embodiments, the feeder cells are OP9. In some embodiments, the feeder cells are K562. In some embodiments, the feeder cell overexpresses one or more cytokines, ligands or receptors that support the differentiation, expansion, and/or functionality of the derivative cells. In one embodiment, the definitive HE is CD34 positive. In one embodiment, the obtained iMDSCs comprise CD45+ cells. In one embodiment, the obtained iMDSCs comprise CD45+CD33+ cells. In some embodiments, the obtained iMDSCs comprise CD45+CD33+CD14+ cells. In yet some other embodiments, the obtained iMDSCs comprise CD45+CD33+PDL1+ cells.

In one embodiment of the method of producing myeloid suppressive cells including iMDSCs from pluripotent stem cells, and the method comprises (1) differentiating and expanding pluripotent stem cells to obtain a mesodermal population by contacting the pluripotent stem cells with a medium comprising a BMP activator, and optionally bFGF; (2) differentiating and expanding the mesodermal population to obtain mesodermal cells with definitive HE potential by contacting the mesodermal population with a medium comprising a BMP activator, a Wnt pathway activator and bFGF; (3) differentiating and expanding the mesodermal cells with definitive HE potential to obtain definitive HE cells by contacting the mesodermal cells with definitive HE potential with a medium comprising a ROCK inhibitor, and one or more of the growth factors and cytokines selected from the group consisting of VEGF, bFGF, SCF, IL6, and IL11; and (4) differentiating and expanding the definitive HE cells to obtain iMDSCs by contacting the definitive HE with a medium comprising a ROCK inhibitor and MCSF, and one or more growth factors and cytokines selected from the group consisting of IL1b, IL3, IL6, IL4, IL10, IL13, TGFβ, bFGF, VEGF, SCF, GMCSF, and FLT3L, and optionally, one or both of an AhR antagonist and a prostaglandin pathway agonist. In some embodiment, the above method further comprises seeding and expanding pluripotent stem cells in a medium comprising a ROCK inhibitor, a GSK3 inhibitor and a MEK inhibitor. In some embodiments, the pluripotent stem cells are iPSCs. In some embodiments, the iPSCs are naïve iPSCs. In some embodiments, the iHE cells obtained from the above method express CD34. In some embodiments, the above method further comprises sorting the obtained iHE cells using CD34, CD43, CD73, and/or CXCR4. In some embodiments, the sorting uses CD34 positive, and CD43 negative. In some embodiments, the sorting uses CD34 positive, CD43 negative, and CD73 negative. In some other embodiments, the sorting uses CD34 positive, CD43 negative, CD73 negative, and CXCR4 negative. In some embodiments, the media in the above method are free, or essentially free, of TGFβ receptor inhibitor. In some embodiments, the BMP activator of the method is BMP4. In some embodiments, the Wnt pathway activator is a GSK3 inhibitor. In some embodiments, contacting cell with a culture medium comprising GSK3 inhibitor is only after mesodermal cell specification in order to achieve definitive HE potential. In some embodiments, the AhR antagonist is StemRegenin1 (SR1). In some embodiments, the prostaglandin pathway agonist is PGE2, or derivatives and analogs thereof. In some embodiments, the method above further comprises subjecting the seeded iPSC, and/or mesodermal cells under a low oxygen tension between about 2% and about 10%. In one embodiment, the obtained iMDSCs comprise CD45$^+$ cells. In one embodiment, the obtained iMDSCs comprise CD45$^+$CD33$^+$ cells. In some embodiments, the obtained iMDSCs comprise CD45$^+$CD33$^+$CD14$^+$ cells. In yet some other embodiments, the obtained iMDSCs comprise CD45$^+$CD33$^+$PDL1$^+$ cells.

In one embodiment of the method, the method enables producing myeloid suppressive cells including iMDSCs from a mesodermal population derived from the pluripotent stem cells, and the method comprises (1) differentiating and expanding the mesodermal population to obtain mesodermal cells with definitive HE potential by contacting the mesodermal population with a medium comprising a BMP activator, a Wnt pathway activator and bFGF; (2) differentiating and expanding the mesodermal cells with definitive HE potential to obtain definitive HE cells by contacting the mesodermal cells with definitive HE potential with a medium comprising a ROCK inhibitor, and one or more of the growth factors and cytokines selected from the group consisting of VEGF, bFGF, SCF, IL6, and IL11; and (3) differentiating and expanding the definitive HE cells to obtain iMDSCs by contacting the definitive HE with a medium comprising a ROCK inhibitor and MCSF, and one or more growth factors and cytokines selected from the group consisting of IL1b, IL3, IL6, IL4, IL10, IL13, TGFβ, bFGF, VEGF, SCF, GMCSF, and FLT3L, and optionally, one or both of an AhR antagonist and a prostaglandin pathway agonist. In one embodiment, the medium composition for generating a population of iMDSCs comprises a ROCK inhibitor, MCSF, IL3, VEGF, bFGF, SCF, and FLT3L. In some embodiments, said medium further comprises one or more of IK1b, IL6, IL10, and TGFβ. In some embodiments, the medium composition does not have IL6. In some embodiments, the medium composition does not require TPO. In some embodiments, the medium composition further comprises feeder cell or feeder cell components. In some embodiments, the feeder cells are OP9. In some embodiments, the feeder cells are K562. In some embodiments, the feeder cell overexpresses one or more cytokines, ligands or receptors that support the differentiation, expansion, and/or functionality of the derivative cells.

In another embodiment of the method, the method enables producing myeloid suppressive cells including iMDSCs from mesodermal cells with definitive HE potential, and the method comprises (1) differentiating and expanding the mesodermal population to obtain mesodermal cells with definitive HE potential by contacting the mesodermal population with a medium comprising a BMP activator, a Wnt pathway activator and bFGF; (2) differentiating and expanding the mesodermal cells with definitive HE potential to obtain definitive HE cells by contacting the mesodermal cells with definitive HE potential with a medium comprising a ROCK inhibitor, and one or more of the growth factors and cytokines selected from the group consisting of VEGF, bFGF, SCF, IL6, and IL11; and (3) differentiating and expanding the definitive HE cells to obtain iMDSCs by contacting the definitive HE with a medium comprising a ROCK inhibitor and MCSF, and one or more growth factors and cytokines selected from the group consisting of IL1b, IL3, IL6, IL4, IL10, IL13, TGFβ, bFGF, VEGF, SCF, GMCSF, and FLT3L, and optionally, one or both of an AhR antagonist and a prostaglandin pathway agonist. In some embodiments, the obtained iMDSCs are further expanded to generate a cell population enriched with, or comprising, an increased number and proportion of monocytic MDSCs. In some embodiments, the percentage of monocytic MDSCs in the obtained iMDSCs is more than about 20%, about 30%, about 40%, about 50%, about 60%, about 70%, about 80%, or about 90%, or any range in between. In some embodiments, the differentiation of definitive HE cells and the expansion of iMDSCs last no less than about 5 days, about 7 days, about 9 days, about 12 days, about 15 days, about 18 days, about 22 days, or about 25 days, or any length of time in between. In some embodiments, the differentiation of definitive HE cells and the expansion of iMDSCs last between about 5 to 25 days, about 6 to 22 days, about 6 to 20 days, about 6 to 18 days, about 7 to 18 days, about 7 to 17 days, about 8 to 17 days, about 9 to 17 days, about 10 to 17 days, about 9 to 16 days, about 8 to 16 days, about 9 to 15 days, about 12 to 15 days, about 10 to 14 days, or any length of period in between.

Other aspects of the disclosed methods herein further include optimized cell freezing media and procedure to maximize induced myeloid suppressive cells including iMDSC viability, recovery and function after thawing; cell manufacturing scaling and increase process yield with optimized time extension for differentiation; and clinic compatibility.

II. Pluripotent Stem or Progenitor Cell Derived Immune Regulatory Cell or Population Thereof The present invention provides immune regulatory cells or subpopulations thereof derived from pluripotent stem cells or hemogenic endothelium. In some embodiments, the derived immune regulatory cells comprise myeloid derived suppressor cells (MDSCs), regulatory T cells, regulatory B cells, macrophages, dendritic cells, or mesenchymal stromal cells.

In some embodiments, the derived immune regulatory cells comprise myeloid derived suppressor cells (MDSCs). In one embodiment, the population of derived immune regulatory cells comprises CD45$^+$CD33$^+$ cells. In some embodiments, the population derived immune regulatory cells comprise at least 10%, 20%, 30%, 40%, 50%, 60%, 70%, 80%, 90%, or more, or any percentage in between, of CD45$^+$CD33$^+$ cells. In some embodiments, the population derived immune regulatory cells comprise no less than 10%, 20%, 30%, 40%, 50%, 60%, 70%, 80%, 90%, or any percentage in between, of CD45$^+$CD33$^+$ cells.

In some embodiments, the population of derived immune regulatory cells comprise monocytes, or monocytic MDSCs. In some embodiments, the monocytes comprise CD45$^+$CD33$^+$CD14$^+$ cells. In some embodiments, the population of derived immune regulatory cells comprise at least 20%, 25%, 30%, 40%, 50%, 60%, 70%, 80%, 90%, or any percentage in between, of monocytes or CD45$^+$CD33$^+$CD14$^+$ cells. In some embodiments, the population derived immune regulatory cells comprise no less than 20%, 30%, 40%, 50%, or any percentage in between, of monocytes or CD45$^+$CD33$^+$CD14$^+$ cells.

In yet some other embodiments, the population of derived immune regulatory cells comprise CD45$^+$CD33$^+$PDL1$^+$ cells. In some embodiments, the population of derived immune regulatory cells comprise at least 20%, 25%, 30%, 40%, 50%, or any percentage in between, of CD45$^+$CD33$^+$PDL1$^+$ cells. In some embodiments, the population derived immune regulatory cells comprise no less than 20%, 30%, 40%, 50%, or any percentage in between, of CD45$^+$CD33$^+$PDL1$^+$ cells.

In some other embodiments, the population of derived immune regulatory cells comprise CD33$^+$CD15$^+$CD14$^-$CD11b$^-$ cells. In some embodiments, the population of derived immune regulatory cells comprise at least 5%, 10%, 15%, 20%, 25%, 30%, 40%, 50%, 60%, 70%, 80%, 90%, or any percentage in between, of CD33$^+$CD15$^+$CD14$^-$CD11b$^-$ cells. In some embodiments, the population derived immune regulatory cells comprise no less than 5%, 10%, 15%, 20%, 30%, 40%, 50%, or any percentage in between, of CD33$^+$CD15$^+$CD14$^-$CD11b cells.

In some embodiments, the population of derived immune regulatory cells comprising iMDSCs comprise less than 50%, 40%, 30%, 20%, 10%, 5%, 2%, 1%, 0.1% of erythrocytes. In some embodiments, the population of derived immune regulatory cells comprising iMDSCs comprise less than 50%, 40%, 30%, 20%, 10%, 5%, 2%, 1%, 0.1% of CD45$^-$CD235$^+$ cells. In some embodiments, the population of derived immune regulatory cells is essentially free of erythrocytes or CD45$^-$CD235$^+$ cells.

In some embodiments, the population of derived immune regulatory cells comprising iMDSCs comprise less than 50%, 40%, 30%, 20%, 10%, 5%, 2%, 1%, or 0.1% of lymphoid. In some embodiments, the population of derived immune regulatory cells comprising iMDSCs comprise less than 50%, 40%, 30%, 20%, 10%, 5%, 2%, 1%, or 0.1% of CD45$^+$CD7$^+$ cells. In some embodiments, the population of derived immune regulatory cells is essentially free of lymphoid or CD45$^+$CD7$^+$ cells.

In some embodiments, the population of derived immune regulatory cells comprising iMDSCs comprise less than 50%, 40%, 30%, 20%, 10%, 5%, 2%, 1%, or 0.1% of lymphoid. In some embodiments, the population of derived immune regulatory cells comprising iMDSCs comprise less than 50%, 40%, 30%, 20%, 10%, 5%, 2%, 1%, or 0.1% of CD45$^+$CD7$^+$ cells. In some embodiments, the population of derived immune regulatory cells is essentially free of lymphoid or CD45$^+$CD7$^+$ cells.

In some embodiments, the population of derived immune regulatory cells comprising iMDSCs comprise less than 50%, 40%, 30%, 20%, 10%, 5%, 2%, 1%, or 0.1% of granulocytes. In some embodiments, the population of derived immune regulatory cells comprising iMDSCs comprise less than 50%, 40%, 30%, 20%, 10%, 5%, 2%, 1%, or 0.1% of CD45$^+$CD33$^+$CD66b$^+$ cells. In some embodiments, the population of derived immune regulatory cells is essentially free of lymphoid or CD45$^+$CD33$^+$CD66b$^-$ cells.

In some other embodiments, the population of derived immune regulatory cells comprising iMDSCs is essentially free of one or more cell subpopulations selected from the group consisting of erythrocytes, lymphoid, and granulocytes.

Another aspect of this invention provides an enriched cell population or subpopulation of immune regulatory cells comprising CD45$^+$CD33$^+$, CD45$^+$CD33$^+$CD14$^+$, or CD45$^+$CD33$^+$PDL1$^+$ cells. As used herein, the term "enriched," or "isolated," or "purified," or "sorted," refers to a cell population comprising more than 50%, 60%, 70%, 80%, 90%, 95%, or more, or any percentage in between, of the cell population or subpopulation of interest.

Yet another aspect of the invention provides derived immuno-regulatory cells comprising iMDSCs, and/or subpopulations thereof, that are genomically engineered, which include insertion, deletion, or nucleic acid replacement. In one embodiment, the genomically engineered immune regulatory cells comprise genetically modified modalities including one or more of: safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the immune regulatory cells. In some embodiments, the immuno-regulatory cells, including iMDSCs, have at least one genomic modification comprising introduced or increased expression of a chimeric receptor, a homing receptor or adhesion molecule, an anti-inflammatory molecule, an immune checkpoint protein, a cytokine/chemokine decoy receptor, a growth factor, an altered pro-inflammatory cytokine receptor, a CAR, or a surface triggering receptor for coupling with bi- or multi-specific or universal engagers; or reduced or silenced expression of a co-stimulatory gene.

In some embodiments, the derived immuno-regulatory cells comprising iMDSCs, and/or subpopulations thereof, comprise an exogenous nucleic acid. In some embodiments, the exogenous nucleic acid is introduced to the immune regulatory cells via direct genomic editing of the cells. In some other embodiments, the exogenous nucleic acid is introduced to the immune regulatory cells via retaining the same from a genomically engineered hematopoietic stem or progenitor cell, iCD34, or iPSC, which gives rise to the immune regulatory cells through differentiation. In some embodiments, the genetically engineered immuno-regulatory cells, including iMDSCs, have one or more enhanced immune-regulatory function such as: enhanced anti-inflammatory signaling; enhanced homing to sites of inflammation; reduced immunogenicity and immune clearance; and enhanced ability in inducing T cell anergy.

In some embodiments of the modified immuno-regulatory cells, including iMDSCs, comprises a chimeric receptor for activating iMDSCs. In one embodiment, the chimeric receptor comprises an extracellular domain, fused to an intracellular domain for anti-inflammatory signaling. In some embodiments of the chimeric receptor, the extracellular domain of the receptor is derived from an antigen specific binding sequence; an immunoglobulin; or a pro-inflammatory cytokine receptor. In some embodiments of the chimeric receptor, the intracellular domain is for anti-inflammatory signaling comprising at least one of IL10R, IL35R, and AhR.

In some embodiments of the modified immuno-regulatory cells, including iMDSCs, wherein the homing receptor or adhesion molecule comprises at least one of CXCR4, CCR2, CCR5, CCR6, CXCR3, CCR7, CD62L, and VLA4.

In some embodiments of the modified immuno-regulatory cells, including iMDSCs, wherein the introduced or increased expression of an anti-inflammatory molecule, an immune checkpoint protein, a cytokine/chemokine decoy receptor and/or a growth factor is driven by a promoter regulated by inflammatory signaling. In some embodiments, the inflammatory signaling comprises TLR or IFNγR signaling. In some embodiments, the promoter is an inducible promoter. In some embodiments, the promoter is triggered only after homing of the iMDSCs. In some embodiments, the engineered expression comprises one or more of IDO1, PDL1, CTLA4, Arg1, IL35, IL10, HO-1, CrmB, Y136, HGFL, GMCSF, and TGFβ.

In some embodiments of the modified immuno-regulatory cells, including iMDSCs, comprise engineered HLA. In one embodiment, HLA 1 or 2 is knocked out. In one embodiment, the modified immuno-regulatory cells comprise a deletion or reduced expression in at least one of B2M, TAP1, TAP2, Tapasin, NLRC5, RFXANK, CIITA, RFX5, RFXAP, and any of the HLA genes in the chromosome 6p21 region. In another embodiment, the modified immuno-regulatory cells comprise an introduced or increased expression of HLA-E or HLA-G. iMDSCs with modified HLA class I and/or II are capable of immune evasion, have increased resistance to immune detection, and/or present improved in vivo persistence. Moreover, such cells can avoid the need for HLA matching in adoptive cell therapy and thus provide a source of universal, off-the-shelf therapeutic regimen. One aspect of the present application provides a method of obtaining such modified iMDSCs from engineered clonal iPSCs. This method provides homogeneous engineered modalities in the derived MDSC population, resulting in significantly lower risk of rejection disorders otherwise caused by unmodified cells that could exist when engineering a primary MDSC population, which is heterogenous in nature. In addition, obtaining MDSCs through iPSC differentiation skews the phenotype of a derived MDSC population to contain significantly increased number and proportion of therapeutically relevant subpopulations such as M-MDSCs, characterized by CD45$^+$, CD33$^+$ and CD14$^+$. Such a derived MDSC population can be further selectively expanded to comprise more than 90% or M-MDSCs in extended culturing as provided herein.

In some embodiments of the modified immuno-regulatory cells, including iMDSCs, comprise one or more altered pro-inflammatory cytokine receptors. In some embodiments, the altered pro-inflammatory cytokine receptor sequesters pro-inflammatory cytokines present in the inflammatory milieu. In some embodiments, the altered pro-inflammatory cytokine receptors are membrane bound. In some embodiments, the altered pro-inflammatory cytokine receptor is in a soluble form. In some embodiments, the sequestered cytokines include, but are not limited to IL2R, IL6R, and IFNγR.

In some embodiments, the population or subpopulation of immune regulatory cells is differentiated in vitro from a stem cell or progenitor cell. In some embodiments, the isolated population or subpopulation of immune regulatory cells can be differentiated from a stem cell, a hematopoietic stem or progenitor cell (HSC), or a progenitor cell. The progenitor cell can be a CD34$^+$ hemogenic endothelium cell. The stem cell can be a pluripotent stem cell, such as induced pluripotent stem cells (iPSCs) and embryonic stem cells (ESCs). The iPSC is a non-naturally occurring reprogrammed pluripotent cell. Once the cells of a subject have been reprogrammed to a pluripotent state, the cells can then be programmed or differentiated to a desired cell type or subtypes, such as MDSCs.

In some embodiments, the iPSC is differentiated to MDSCs by a multi-stage differentiation platform wherein cells from various stages of development can be induced to hemogenic endothelium cells that express CD34 (See e.g. U.S. Applications 62/107,517 and 62/251,016, the disclosures of which are incorporated herein in their entireties), which are further differentiated according to methods of this application to assume an immune regulatory cell phenotype. In some embodiments, the iPSC or iCD34 for regulatory cell differentiation is genomically engineered, which include insertion, deletion, or nucleic acid replacement.

In some embodiments, the genomically engineered iPS or iCD34 cells comprise genetically modified modalities including one or more of: safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the immune regulatory cells. In some embodiments, the genomically engineered iPS or iCD34 cells have at least one genomic modification comprising introduced or increased expression of a chimeric receptor, a homing receptor, an anti-inflammatory molecule, an immune checkpoint protein, a cytokine/chemokine decoy receptor, a growth factor, an altered pro-inflammatory cytokine receptor, a CAR, or a surface triggering receptor for coupling with bi- or multi-specific or universal engagers; or reduced or silenced expression of a co-stimulatory gene. In some embodiments, the genomically engineered iPS or iCD34 cells comprise an exogenous nucleic acid. In some embodiments, the exogenous nucleic acid is introduced to the iPS or iCD34 cells via direct genomic editing of the iPS or iCD34 cells. In some other embodiments, the exogenous nucleic acid comprised in the iCD34 cells is introduced to the iCD34 cells via retaining the same from a genomically engineered iPS cells used for differentiation. In some other embodiments, the exogenous nucleic acid comprised in the iPS cells is introduced to the iPS via retaining the same from a genomically engineered somatic or non-pluripotent cells used for reprogramming to obtain the iPS cells. In some embodiments, the somatic or non-pluripotent cells used for reprogramming to obtain the iPS cells are obtained from a subject who has been previously administered genetically modified immune cells. In some embodiments, the previously administered genetically modified immune cells comprise an exogenous nucleic acid encoding a T Cell Receptor (TCR) and/or a Chimeric Antigen Receptor (CAR).

Various strategies are being pursued to induce pluripotency, or increase potency, in cells (Takahashi, K., and Yamanaka, S., Cell 126, 663-676 (2006); Takahashi et al., Cell 131, 861-872 (2007); Yu et al., Science 318, 1917-1920 (2007); Zhou et al., Cell Stem Cell 4, 381-384 (2009); Kim et al., Cell Stem Cell 4, 472-476 (2009); Yamanaka et al., 2009; Saha, K., Jaenisch, R., Cell Stem Cell 5, 584-595 (2009)), and improve the efficiency of reprogramming (Shi et al., Cell Stem Cell 2, 525-528 (2008a); Shi et al., Cell Stem Cell 3, 568-574 (2008b); Huangfu et al., Nat Biotechnol 26, 795-797 (2008a); Huangfu et al., Nat Biotechnol 26, 1269-1275 (2008b); Silva et al., Plos Bio 6, e253. Doi: 10.1371/journal. Pbio. 0060253 (2008); Lyssiotis et al., PNAS 106, 8912-8917 (2009); Ichida et al., Cell Stem Cell 5, 491-503 (2009); Maherali, N., Hochedlinger, K., Curr Biol 19, 1718-1723 (2009b); Esteban et al., Cell Stem Cell 6, 71-79 (2010); and Feng et al., Cell Stem Cell 4, 301-312 (2009)), the disclosures of which are hereby incorporated by reference in their entireties.

In some embodiments, the modified iPS or iCD34 cells for deriving immune regulatory cells including iMDSCs, comprise a MDSC activating chimeric receptor. In one embodiment, the chimeric receptor comprises an extracellular domain, fused to an intracellular domain for anti-inflammatory signaling. In some embodiments of the chimeric receptor, the extracellular domain of the receptor is derived from an antigen specific binding sequence; an immunoglobulin; or a pro-inflammatory cytokine receptor. In some embodiments of the chimeric receptor, the intracellular domain is for anti-inflammatory signaling comprising at least one of IL10R, IL35R, and AhR.

In some embodiments, the modified iPS or iCD34 cells for deriving immune regulatory cells including iMDSCs, comprise one or more homing receptor or adhesion molecule comprising CXCR4, CCR2, CCR5, CCR6, CXCR3, CCR7, CD62L, or VLA4.

In some embodiments, the modified iPS or iCD34 cells for deriving immune regulatory cells including iMDSCs, comprise an introduced or increased expression of an anti-inflammatory molecule, an immune checkpoint protein, a cytokine/chemokine decoy receptor and/or a growth factor driven by a promoter regulated by inflammatory signaling. In some embodiments, the inflammatory signaling comprises TLR or IFNγR signaling. In some embodiments, the promoter is an inducible promoter. In some embodiments, the promoter is triggered only after homing of the iMDSCs. In some embodiments, the engineered expression comprises one or more of IDO1, PDL1, CTLA4, Arg1, IL35, IL10, HO-1, CrmB, Y136, HGFL, GMCSF, and TGFβ.

In some embodiments, the modified iPS or iCD34 cells for deriving immune regulatory cells including iMDSCs, comprise engineered HLA. In one embodiment, HLA 1 or 2 is knocked out in modified iPS or iCD34. In one embodiment, the modified iPS or iCD34 cells comprise a deletion or reduced expression in at least one of B2M, TAP1, TAP2, Tapasin, NLRC5, RFXANK, CIITA, RFX5, RFXAP, and any of the HLA genes in the chromosome 6p21 region. In another embodiment, the modified iPS or iCD34 cells comprise an introduced or increased expression of HLA-E or HLA-G.

In some embodiments of the modified iPS or iCD34 cells for deriving immuno-regulatory cells, including iMDSCs, comprise one or more altered pro-inflammatory cytokine receptors. In some embodiments, the altered pro-inflammatory cytokine receptor sequesters pro-inflammatory cytokines present in the inflammatory milieu. In some embodiments, the altered pro-inflammatory cytokine receptors are membrane bound. In some embodiments, the altered pro-inflammatory cytokine receptor is in a soluble form. In some embodiments, the sequestered cytokines include, but are not limited to IL2R, IL6R, and IFNγR.

Another aspect of this invention provides modulated immune regulatory cells or subpopulations thereof, wherein the immune regulatory cells are derived from pluripotent stem cells or hemogenic endothelium, wherein the population or subpopulation of immune regulatory cells have been contacted with one or more modulating agents, and wherein the modulated immune regulatory cells have improved therapeutic potential in comparison to the cells without the modulation. In some embodiments, the modulated immune regulatory cells comprise modulated myeloid derived suppressor cells (MDSCs). The modulation with one or more of said agents can modify the biological properties of the immune regulatory cells to improve cell proliferation, survival, persistence, homing, and/or immune regulatory function.

As used interchangeably herein, "modulators" or "modulating agents" are used to refer to inhibitory or activating agents identified using in vitro and in vivo assays for their ability to regulate the expression or activity of a particular target (protein or encoding polynucleotide). "Modulators" or "modulating agents" include inhibitors and activators, e.g., ligands, agonists, antagonists. A modulating agent, or a modulator, as used herein may be an organic compound (e.g., small chemical molecules), a polypeptide (e.g., a peptide or an antibody), a nucleic acid (e.g., DNA, RNA, double-stranded, single-stranded, an oligonucleotide, anti-sense RNA, small inhibitory RNA, micro RNA, a ribozyme, etc.), an oligosaccharide, or a lipid; or their similarly functioning (e.g. inhibition or activation towards the same target) homologs, mimetics, derivatives, analogues or salts, whether synthetic or naturally occurring.

Inhibitors are agents that may, e.g., decrease or eliminate the expression of a described target protein; or partially or totally block stimulation or protease inhibitor activity of the target protein; or decrease, prevent, delay activation, inactivate, desensitize, or down regulate the activity of the target protein, e.g., antagonists. Activators are agents that may, e.g., induce or activate the expression of a described target protein, or stimulate, increase, activate, facilitate, enhance activation or protease inhibitor activity, sensitize or up regulate the activity of described target protein, e.g., agonists. Assays for inhibitors and activators include, e.g., applying putative modulator agents to cells expressing the described target protein and then determining the functional effects and extent of the effect on the described target protein expression and/or activity. Generally, control samples (untreated with modulators or treated with vehicle alone) are assigned a specific activity value of 100%. Inhibition of a described target protein is achieved when the activity value relative to the control is about 90%, optionally 80%, 70%, 60%, 50%, 25%, 10%, 5% or 1% or lower. Activation of the described target protein is achieved when the activity value relative to the control is 110%, optionally 150%, 200%, 300%, 400%, 500%, or 1000-3000% or higher.

To improve immune regulatory cell therapeutic potential generally requires certain improvements in the quality of the cells. Treatment with selected modulating agent(s) could enhance the biological properties of the treated immune regulatory cells by modulating at least one of the following: cell phenotype skewing, expansion, maintenance, survival, proliferation, persistence, and/or T cell suppression, thereby improving the therapeutic potential of the immune regulatory cells. In a MDSC population, for example, phenotype skewing towards an increased number or relative ratio of one cell subpopulation that are more functional and effective in suppressing T cell proliferation and/or T cell effector function results in improved therapeutic potential in the MDSC population. In one embodiment, the monocytes comprised in a MDSC population is increased in number or relative ratio after modulation. In another embodiment, the $CD45^+CD33^{30}\,PDL1^+$ subpopulation comprised in a MDSC population is increased in number or relative ratio after modulation.

In some embodiments, the selected modulating agent comprises one or more small molecule compounds. In some embodiments, the method of modulating a population or a subpopulation of immune regulatory cells suitable for adoptive cell-based therapies comprises contacting the cells with a composition comprising at least one said agent in a sufficient amount to improve at least one desirable therapeutic attribute in comparison to immune regulatory cells without contacting the same composition. In one embodiment, the modulating agent for immune regulatory cell treatment is between about 0.1 nM to about 50 μM. In one embodiment, the agent for immune cell treatment is about 0.1 nM, 0.5 nM, 1 nM, 5 nM, 10 nM, 50 nM, 100 nM, 500 nM, 1 μM, 5 μM, 10 μM, 20 μM, or 25 μM, or any concentration in-between. In one embodiment, the modulating agent for immune regulatory cell treatment is about 0.1 nM to about 5 nM, is between about 1 nM to about 100 nM, is between about 50 nM to about 250 nM, between about 100 nM to about 500 nM, between about 250 nM to about 1 μM, between about 500 nM to about 5 μM, between about 3 μM to about 10 μM, between about 5 μM to about 15 μM, between about 12 μM to about 20 μM, or between about 18 μM to about 25 μM, or any range in-between.

In some embodiments, the method of modulating a population or a subpopulation of immune regulatory cells suitable for adoptive cell-based therapies comprises contacting the immune regulatory cells with a composition comprising at least one modulating agent for a sufficient length of time to improve at least one desirable therapeutic attribute in comparison to immune regulatory cells without contacting the same composition. In one embodiment, the immune regulatory cells are contacted with one or more of said agents for at least 10 minutes, 30 minutes, 1 hours, 2, hours, 5 hours, 12 hours, 16 hours, 18 hours, 1 day, 2 days, 3 days, 4 days, 5 days, 6 days, 7 days, 10 days, 15 days, 20 days, 25 days, 30 days, or any length of period in between. In one embodiment, the immune cells are contacted with one or more of said agents for between about 0.5 hour to about 2 hours, between about 1 hour to about 12 hours, between about 10 hours to about 2 days, between about 1 day to about 3 days, between about 2 days to about 5 days, between about 3 days to about 6 days, between about 5 days to about 8 days, between about 7 days to about 14 days, between about 12 days to about 22 days, between about 14 days to about 25 days, between about 20 days to about 30 days. In some embodiments, the immune cells are contacted with one or more of said agents for no less than 16 hours, 14 hours, 12 hours, 10 hours, 8 hours, 6 hours, 4 hours, 2 hours, or any length of time in between. As such, said sufficient length of time, for example, is no less than 15, 13, 11, 9, 7, 5, 3, or 1 hour(s). In some other embodiments of the method, said sufficient length of time is no less than 24 hours, 36 hours, 48 hours, 60 hours, 72 hours, or any length of time in between. As such, said sufficient length of time is, for example, no less than 30, 42, 54, 66, 78, 90 hour(s).

The method of modulating a population or a subpopulation of immune regulatory cells suitable for adoptive cell-based therapies that comprises contacting the immune regulatory cells with a composition comprising at least one said agent, may further comprise enriching or isolating one or more desired subpopulations from the immune regulatory cells after the contact, wherein the one or more desired subpopulations comprise $CD45^+CD33^+$, $CD45^+CD33^+CD14^+$, and/or $CD45^+CD33^+PDL1^+$.

Still another aspect of the present invention provides a therapeutic composition. In some embodiments, the derived immune regulatory cells, optionally with genetic modification and/or agent modulation, may be administered autologously or allogeneically.

Also provided herein is a combinational therapeutic composition comprising the immune regulatory cells as disclosed and one or more therapeutic additives/agents. In some embodiments of the combinational therapeutic composition, the one or more therapeutic additives comprise a peptide, a cytokine, a mitogen, a growth factor, a small RNA, a dsRNA (double stranded RNA), mononuclear blood cells, feeder cells, feeder cell components or replacement factors thereof, a vector comprising one or more polynucleic acids of interest, an antibody, a chemotherapeutic agent or a radioactive moiety, or an immunomodulatory drug (IMiD).

In some embodiments, the additional therapeutic agent comprises an antibody, or an antibody fragment. In some embodiments, the antibody may be a humanized antibody, a humanized monoclonal antibody, a chimeric antibody. In some embodiments, the antibody, or antibody fragment, specifically binds to a viral antigen. In other embodiments, the antibody, or antibody fragment, specifically binds to a tumor antigen. In some embodiments, the tumor or viral specific antigen activates the modulated cells to better interact with their target cells.

As used herein, chemotherapeutic agent refers to cytotoxic antineoplastic agents, that is, chemical agents which preferentially kill neoplastic cells or disrupt the cell cycle of rapidly-proliferating cells, or which are found to eradicate stem cancer cells, and which are used therapeutically to prevent or reduce the growth of neoplastic cells. Chemotherapeutic agents are also sometimes referred to as antineoplastic or cytotoxic drugs or agents, and are well known in the art. In some embodiments, the chemotherapeutic agent comprises an anthracycline, an alkylating agent, an alkyl sulfonate, an aziridine, an ethylenimine, a methylmelamine, a nitrogen mustard, a nitrosourea, an antibiotic, an antimetabolite, a folic acid analog, a purine analog, a pyrimidine analog, an enzyme, a podophyllotoxin, a platinum-containing agent, an interferon, a vinca alkaloid, an epipodophyllotoxin, or an interleukin. Exemplary chemotherapeutic agents include, but are not limited to, cyclophosphamide, mechlorethamine, mephalin, chlorambucil, heamethylmelamine, thiotepa, busulfan, carmustine, lomustine, semustine, methotrexate, fluorouracil, floxuridine, cytarabine, 6-mercaptopurine, thioguanine, pentostatin, vincristine, vinblastine, vindesine, etoposide, etoposide orthoquinone, teniposide, daunorubicin, doxorubicin, mitoxantrone, bisanthrene, actinomycin D, plicamycin, puromycin, gramicidine D, paclitaxel, colchicine, cytochalasin B, emetine, maytansine, and amsacrine. Additional agents include aminglutethimide, cisplatin, carboplatin, mitomycin, altretamine, cyclophosphamide, lomustine (CCNU), carmustine (BCNU), irinotecan (CPT-11), alemtuzamab, altretamine, anastrozole, L-asparaginase, azacitidine, bevacizumab, bexarotene, bleomycin, bortezomib, busulfan, calusterone, capecitabine, celecoxib, cetuximab, cladribine, clofurabine, cytarabine, dacarbazine, denileukin diftitox, diethlstilbestrol, docetaxel, dromostanolone, epirubicin, erlotinib, estramustine, etoposide, ethinyl estradiol, exemestane, floxuridine, 5-flourouracil, fludarabine, flutamide, fulvestrant, gefitinib, gemcitabine, goserelin, hydroxyurea, ibritumomab, idarubicin, ifosfamide, imatinib, interferon alpha (2a, 2b), irinotecan, letrozole, leucovorin, leuprolide, levamisole, meclorethamine, megestrol, melphalin, mercaptopurine, methotrexate, methoxsalen, mitomycin C, mitotane, mitoxantrone, nandrolone, nofetumomab, oxaliplatin, paclitaxel, pamidronate, pemetrexed, pegademase, pegasparagase, pentostatin, pipobroman, plicamycin, polifeprosan, porfimer, procarbazine, quinacrine, rituximab, sargramostim, streptozocin, tamoxifen, temozolomide, teniposide, testolactone, thioguanine, thiotepa, topetecan, toremifene, tositumomab, trastuzumab, tretinoin, uracil mustard, valrubicin, vinorelbine, and zoledronate.

Other suitable agents are those that are approved for human use, including those that will be approved, as chemotherapeutics or radiotherapeutics, and known in the art. Such agents can be referenced through any of a number of standard physicians' and oncologists' references (e.g. Goodman & Gilman's *The Pharmacological Basis of Therapeutics*, Ninth Edition, McGraw-Hill, N.Y., 1995) or through the National Cancer Institute website (fda.gov/cder/cancer/druglistframe.htm), both as updated from time to time. Immunomodulatory drugs (IMiDs) such as thalidomide, lenalidomide, and pomalidomide stimulate both NK cells and T cells. As provided herein, IMiDs may be used with the modulated therapeutic immune regulatory cells for cancer treatments.

III. Therapeutic Use of the Immune Regulatory Cells, Cell Population or Subpopulations The present invention also provides methods of treating a subject, i.e., inhibiting, preventing, ameliorating a condition, by using immune regulatory cells derived in vitro from pluripotent stem or progenitor cells, and optionally, by one or more additional therapeutic agents as described. In some embodiments, the derived immune regulatory cells comprise at least one genetic modification. In some other embodiments, the derived immune regulatory cells have been contacted with one or more modulating agents.

In one aspect, the derived immune regulatory cells can be used to treat, prevent, or ameliorate conditions and diseases associated with inflammatory cell activation. "Inflammatory cell activation" refers to the induction by a stimulus (including but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including but not limited to, major histocompatability antigens or cell adhesion molecules) in inflammatory cells (including but not limited to monocytes, macrophages, T lymphocytes, B lymphocytes, granulocytes (polymorphonuclear leukocytes including neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory condition.

An inflammatory condition or disease includes, but is not limited to including but not limited to arthritic diseases such as rheumatoid arthritis (RA), osteoarthritis, gouty arthritis, spondylitis, and reactive arthritis; Behcet's syndrome; sepsis; septic shock; endotoxic shock; gram negative sepsis; gram positive sepsis; toxic shock syndrome; multiple organ injury syndrome secondary to septicemia, trauma, or hemorrhage; ophthalmic disorders including but not limited to allergic conjunctivitis, vernal conjunctivitis, uveitis, and thyroid-associated ophthalmopathy; eosinophilic granuloma; pulmonary or respiratory conditions including but not limited to asthma, chronic bronchitis, allergic rhinitis, adult respiratory distress syndrome (ARDS), severe acute respiratory syndrome (SARS), chronic pulmonary inflammatory diseases (e.g., chronic obstructive pulmonary disease), silicosis, pulmonary sarcoidosis, pleurisy, alveolitis, vasculitis, pneumonia, bronchiectasis, hereditary emphysema, and pulmonary oxygen toxicity; ischemic-reperfusion injury, e.g., of the myocardium, brain, or extremities; fibrosis including but not limited to cystic fibrosis; keloid formation or scar tissue formation; atherosclerosis; autoimmune diseases including but not limited to systemic lupus erythematosus (SLE), lupus nephritis, autoimmune thyroiditis, multiple sclerosis, some forms of diabetes, and Reynaud's syndrome; tissue or organ transplant rejection disorders including but not limited to graft versus host disease (GvHD) and allograft rejection; chronic or acute glomerulonephritis; inflammatory bowel diseases including but not limited to Crohn's disease, ulcerative colitis and necrotizing enterocolitis; inflammatory dermatitis including but not limited to contact dermatitis, atopic dermatitis, psoriasis, and urticaria; fever and myalgias due to infection; central or peripheral nervous system inflammatory conditions including but not limited to meningitis (e.g., acute purulent meningitis), encephalitis, and brain or spinal cord injury due to minor trauma; Sjorgren's syndrome; diseases involving leukocyte diapedesis; alcoholic hepatitis; bacterial pneumonia; community acquired pneumonia (CAP); neumocystis carinii pneumonia (PCP); antigen-antibody complex mediated diseases; hypovolemic shock; Type I diabetes mellitus; acute and delayed hypersensitivity; disease states due to leukocyte dyscrasia and metastasis; thermal injury; granulocyte transfusion associated syndromes; cytokine-induced toxicity; stroke; pancreatitis; myocardial infarction, respiratory syncytial virus (RSV) infection; and spinal cord injury.

The treatment using the immune regulatory cells of this invention could be carried out upon symptom, or for relapse prevention. The terms "treating," "treatment," and the like are used herein to generally mean obtaining a desired pharmacologic and/or physiologic effect. The effect may be prophylactic in terms of completely or partially preventing a disease and/or may be therapeutic in terms of a partial or complete cure for a disease and/or adverse effect attributable to the disease. "Treatment" as used herein covers any treatment of a disease in a mammal, and includes: preventing the disease from occurring in a subject which may be predisposed to the disease but has not yet been diagnosed as having it; inhibiting the disease, i.e., arresting its development; or relieving the disease, i.e., causing regression of the disease. The therapeutic agent or composition may be administered before, during or after the onset of a disease or an injury. The treatment of ongoing disease, where the treatment stabilizes or reduces the undesirable clinical symptoms of the patient, is also of particular interest. In particular embodiments, the subject in need of a treatment has a disease, a condition, and/or an injury that can be treated, ameliorated, and/or improved in at least one associated symptom by a cell therapy. Certain embodiments contemplate that a subject in need of cell therapy, includes, but is not limited to, a candidate for bone marrow or stem cell transplantation, a subject who has received chemotherapy or irradiation therapy, a subject who has or is at risk of having a hyperproliferative disorder or a cancer, e.g. a hyperproliferative disorder or a cancer of hematopoietic system, a subject having or at risk of developing a tumor, e.g., a solid tumor, a subject who has or is at risk of having a viral infection or a disease associated with a viral infection.

The therapeutic composition comprising the derived immune regulatory cells as disclosed can be administered in a subject before, during, and/or after other treatments. As such the method of a combinational therapy can involve the administration or preparation of modulated cells before, during, and/or after the use of an additional therapeutic agent. As provided above, the one or more additional therapeutic agents comprise a peptide, a cytokine, a mitogen, a growth factor, a small RNA, a dsRNA (double stranded RNA), mononuclear blood cells, feeder cells, feeder cell components or replacement factors thereof, a vector comprising one or more polynucleic acids of interest, an antibody, a chemotherapeutic agent or a radioactive moiety, or an immunomodulatory drug (IMiD). The administration of the modulated immune cells can be separated in time from the administration of an additional therapeutic agent by hours, days, or even weeks. Additionally, or alternatively, the administration can be combined with other biologically active agents or modalities such as, but not limited to, an antineoplastic agent, a non-drug therapy, such as, surgery.

As a person of ordinary skill in the art would understand, both autologous and allogeneic immune regulatory cells can be modulated and used in cell therapies as described above.

In some embodiments, the number of derived immune regulatory cells in the therapeutic composition is at least $0.1 \times 10^5$ cells, at least $1 \times 10^5$ cells, at least $5 \times 10^5$ cells, at least $1 \times 10^6$ cells, at least $5 \times 10^6$ cells, at least $1 \times 10^7$ cells, at least $5 \times 10^7$ cells, at least $1 \times 10^8$ cells, at least $5 \times 10^8$ cells, at least $1 \times 10^9$ cells, or at least $5 \times 10^9$ cells.

In some embodiments, the number of derived immune regulatory cells in the therapeutic composition is about $0.1 \times 10^5$ cells to about $1 \times 10^6$ cells; about $0.5 \times 10^6$ cells to about $1 \times 10^7$ cells; about $0.5 \times 10^7$ cells to about $1 \times 10^8$ cells; about $0.5 \times 10^8$ cells to about $1 \times 10^9$ cells; about $1 \times 10^9$ cells to about $5 \times 10^9$ cells; about $0.5 \times 10^9$ cells to about $8 \times 10^9$ cells, or any range in-between.

In some embodiments, the number of derived immune regulatory cells in the therapeutic composition is about $0.5 \times 10^6$ cells to about $1 \times 10^6$ cells; about $0.5 \times 10^7$ cells to about $1 \times 10^7$ cells; about $0.5 \times 10^8$ cells to about $1 \times 10^8$ cells; about $0.5 \times 10^9$ cells to about $5 \times 10^9$ cells; about $1 \times 10^9$ cells to about $8 \times 10^9$ cells, or any range in-between.

In some other embodiments, the number of derived immune regulatory cells in the therapeutic composition is about $0.1 \times 10^5$ cells to about $0.5 \times 10^6$ cells; about $0.5 \times 10^6$ cells to about $0.5 \times 10^7$ cells; about $0.5 \times 10^7$ cells to about $0.5 \times 10^8$ cells; about $0.5 \times 10^8$ cells to about $0.5 \times 10^9$ cells; about $0.5 \times 10^9$ cells to about $8 \times 10^9$ cells, or any range in-between.

In one embodiment, the number of derived immune regulatory cells in the therapeutic composition is the number of immune cells in a partial or single cord of blood, or is at least $0.1 \times 10^5$ cells/kg of bodyweight, at least $0.5 \times 10^5$ cells/kg of bodyweight, at least $1 \times 10^5$ cells/kg of bodyweight, at least $5 \times 10^5$ cells/kg of bodyweight, at least $10 \times 10^5$ cells/kg of bodyweight, at least $0.75 \times 10^6$ cells/kg of bodyweight, at least $1.25 \times 10^6$ cells/kg of bodyweight, at least $1.5 \times 10^6$ cells/kg of bodyweight, at least $1.75 \times 10^6$ cells/kg of bodyweight, at least $2 \times 10^6$ cells/kg of bodyweight, at least $2.5 \times 10^6$ cells/kg of bodyweight, at least $3 \times 10^6$ cells/kg of bodyweight, at least $4 \times 10^6$ cells/kg of bodyweight, at least $5 \times 10^6$ cells/kg of bodyweight, at least $10 \times 10^6$ cells/kg of bodyweight, at least $15 \times 10^6$ cells/kg of bodyweight, at least $20 \times 10^6$ cells/kg of bodyweight, at least $25 \times 10^6$ cells/kg of bodyweight, at least $30 \times 10^6$ cells/kg of bodyweight, $1 \times 10^8$ cells/kg of bodyweight, $5 \times 10^8$ cells/kg of bodyweight, or $1 \times 10^9$ cells/kg of bodyweight, or $8 \times 10^9$ cells/kg of bodyweight.

The derived immune regulatory cells provided by the invention can be administered to a subject without being expanded ex vivo or in vitro prior to administration. In particular embodiments, the modulated population of derived immune regulatory cells can be washed to remove the modulating agent(s).

The therapeutic compositions suitable for administration to a patient can include one or more pharmaceutically acceptable carriers (additives) and/or diluents (e.g., pharmaceutically acceptable medium, for example, cell culture medium), or other pharmaceutically acceptable components. Pharmaceutically acceptable carriers and/or diluents are determined in part by the particular composition being administered, as well as by the particular method used to administer the therapeutic composition. Accordingly, there is a wide variety of suitable formulations of therapeutic compositions of the present invention (see, e.g., Remington's Pharmaceutical Sciences, $17^{th}$ ed. 1985, the disclosure of which is hereby incorporated by reference in its entirety).

In particular embodiments, therapeutic cell compositions having an isolated population of immune regulatory cells also have a pharmaceutically acceptable cell culture medium, or pharmaceutically acceptable carriers and/or diluents. A therapeutic composition comprising a population of immune regulatory cells as disclosed herein can be administered separately by intravenous, intraperitoneal, enteral, or tracheal administration methods or in combination with other suitable compounds to effect the desired treatment goals.

These pharmaceutically acceptable carriers and/or diluents can be present in amounts sufficient to maintain a PH of the therapeutic composition of between about 3 and about 10. As such, the buffering agent can be as much as about 5% on a weight to weight basis of the total composition. Electrolytes such as, but not limited to, sodium chloride and potassium chloride can also be included in the therapeutic composition. In one aspect, the PH of the therapeutic composition is in the range from about 4 to about 10. Alternatively, the PH of the therapeutic composition is in the range from about 5 to about 9, from about 6 to about 9, or from about 6.5 to about 8. In another embodiment, the therapeutic composition includes a buffer having a PH in one of said PH ranges. In another embodiment, the therapeutic composition has a PH of about 7. Alternatively, the therapeutic composition has a PH in a range from about 6.8 to about 7.4. In still another embodiment, the therapeutic composition has a PH of about 7.4.

The invention also provides, in part, the use of a pharmaceutically acceptable cell culture medium in particular compositions and/or cultures of the present invention. Such compositions are suitable for administration to human subjects. Generally speaking, any medium that supports the maintenance, growth, and/or health of the modulated immune cells of the invention are suitable for use as a pharmaceutical cell culture medium. In particular embodiments, the pharmaceutically acceptable cell culture medium is a serum free, and/or feeder-free medium.

In various embodiments, the serum-free medium is animal-free, and can optionally be protein-free. Optionally, the medium can contain biopharmaceutically acceptable recombinant proteins. Animal-free medium refers to medium wherein the components are derived from non-animal sources. Recombinant proteins replace native animal proteins in animal-free medium and the nutrients are obtained from synthetic, plant or microbial sources. Protein-free medium, in contrast, is defined as substantially free of protein. One having ordinary skill in the art would appreciate that the above examples of media are illustrative and in no way limit the formulation of media suitable for use in the present invention and that there are many suitable media known and available to those in the art.

EXAMPLES

The following examples are offered by way of illustration and not by way of limitation.

Example 1—Manufacturing Myeloid Derived Suppressor Cells from Induced Pluripotent Stem Cells To initiate differentiation towards the hematopoietic lineage, hiPSCs were seeded as a monolayer on Day (D) 0 in the maintenance medium containing small molecules comprising ROCK inhibitor, MEK inhibitor and GSK3 inhibitor, and allowed to adhere and expand for about 24 hours. There was no formation of EB in this process. At D1, the maintenance medium was removed and replaced with base medium (for example, containing StemPro 34, glutamine, non-essential amino acids (NEAA), ascorbic acid, and monothioglycerol (MTG)) without the combination of small molecules. Hematopoietic differentiation was initiated at around D2 by switching the culture medium to iCD34-A (for example, comprising base medium, and BMP4). At D3, the culture medium was supplemented with the growth factor bFGF and switched to iCD34-B medium (for example, comprising base medium, BMP4, bFGF, and GSK3 inhibitor) subsequently for differentiation. The monolayers were maintained until around D5-D6 at which point they were dissociated into single cells and seeded as a low density monolayer in iCD34-C medium (for example, comprising base medium, a ROCK inhibitor, bFGF, VEGF, SCF, IL6, and IL11) until differentiation around D10. Low oxygen tension (2-10% $O_2$) was maintained from the onset of hematopoietic differentiation around D2 up until around D10 of differentiation.

During the culture process, the directed differentiation towards the hematopoietic lineage was monitored by the dissociation of the monolayers into single cells and analysis for the surface marker expression of CD34, and optionally, CD43, CD45, CXCR4 and CD73. At around D8 of differentiation, the appearance of a cell population representing HE (hemogenic endothelium) was observed by the cell surface expression signature $CD34^+$. $CD43^-CXCR4^-CD73^+$ was also observed in the $CD34^+$ cells. The iCD34 (i.e. iPSC derived CD34 cells) population was maintained until around D10. At D10, which time point can be shortened to about D9 or extended until about D12, the cells were dissociated into single cells and the iCD34 cell population was sorted by FACS, and then cryopreserved.

For myeloid lineage cell differentiation, freshly thawed iCD34 cells were plated (day 1) on Matrigel coated plates at $7.5\times10^4$ cells per well of a 12 well plate in myeloid differentiation media (for example, comprising base medium, VEGF, bFGF, SCF, IL3, FLT3L, MCSF, GMCSF, StemRegenin1 (SR1), and ROCK inhibitor). On day 2, 4, 6, 8 of culture, 1 ml of myeloid differentiation media without supplementation with Rock inhibitor was added to each well. On day 9, non-adherent cells were harvested through serial rinsing of each well, which can be further cultured, expanded, and enriched. As shown in FIG. 1A, parental human induced pluripotent stem cells (hiPSCs) were differentiated through an approximate 10-day multi-staged monolayer culture process to $CD34^+$ hemogenic endothelium (HE, or iCD34). D10 $iCD34^+$ HE cells cultured in myeloid promoting conditions resulted in $CD45^+$ cells emerging from the endothelial layer starting day 3 after plating and acquiring CD33 by day 9.

To characterize the collected $CD45^+CD33^+$ cells manufactured using this approximate 19-day process, the cells were seeded in a round bottom 96 well plate at $10\times10^4$ cells per well. Cells were treated with human Fc block (BD, 564219) at a 1:200 concentration for 30 minutes at 4° C. Cells were then washed in BD Stain Buffer (BD, 554657) and incubated with the myeloid or erythroid antibody panels for 30 minutes at 4° C. The myeloid antibody panel includes CD45-BV786, CD16-BUV395, CD33-APC, CD1c-BV421, CD14-PerCP-Cy5.5, CD66b-FITC, PDL1-PECy7, CD141-BB515, and Live Dead-APCcy7 antibodies. The erythroid antibody panel includes CD45-BV786, CD71-PE, CD235a-PEcy7, CD144-APC, CD7-BV421, CD43-BV510, CD123-PCP5.5, and Live Dead-APCcy7 antibodies. After incubation, cells were then washed and assessed by flow cytometry on an LSRII (BD) flow cytometer. The characterization of the collected $CD45^+CD33^+$ cells was also conducted using BioLegend LEGENDScreen™ antibody panels.

Figure 1B:
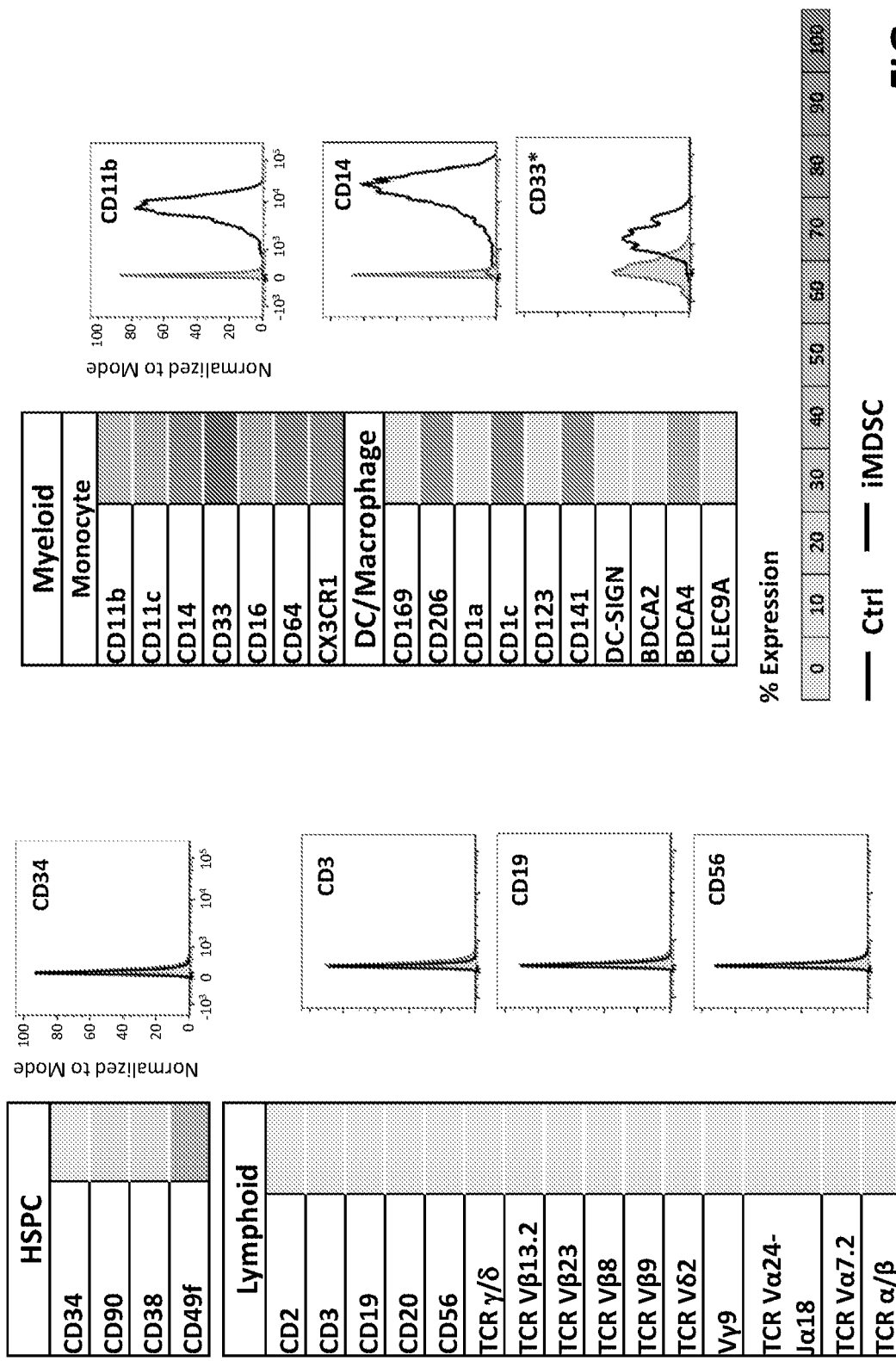
Figure 1C:
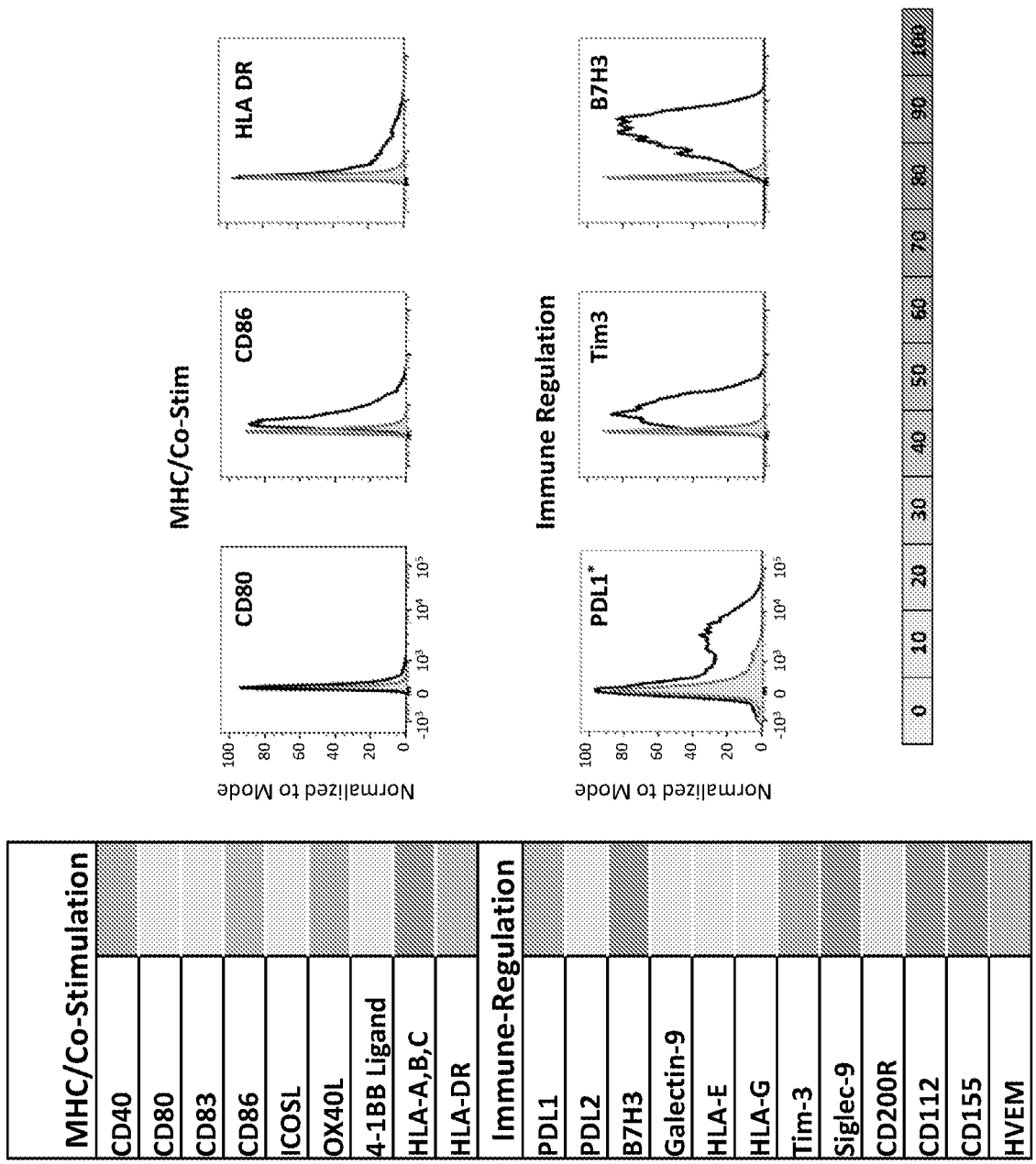

This unbiased immunophenotyping approach demonstrates that day 9 $CD45^+$ cells express predominantly early myeloid markers (e.g. CD33) associated with monocyte populations (e.g. CD14) and are mostly free of lymphoid lineage cells (e.g. CD3 and CD20) (FIG. 1B). In addition, day 9 $CD45^+$ cells express several immune-regulatory surface proteins (e.g. PD-L1, CD112, Siglec9) and have reduced levels of the MEW class II cell surface receptor HLADR and the co-stimulatory molecule CD80 (FIG. 1C). The surface marker profile of day 9 $CD45^+CD33^+$ cells shares significant similarities with that of naturally existing but rarely found immune-regulatory monocytic-myeloid drived suppressor cells (M-MDSC) in healthy individual, both of which are characterized by $CD33^+CD14^+$, and additionally with $CD11b^+$, $CD66^-$, and/or $HLADR^{low}$. In light of these similarities $CD45^+$ cells manufactured using the multi-day process outlined herein are termed iMDSCs.

Figures 1D, 1E:
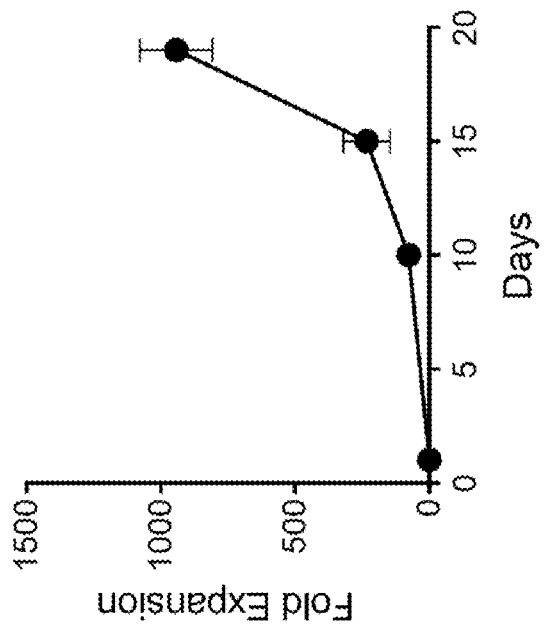

As further shown in FIG. 1D, the $CD45^+CD33^+$ cells derived from iCD34 cells through the multi-day process is highly enriched for myeloid markers (>90% purity) and is substantially free of granulocytes ($CD45^+CD33^+CD66b^+$), erythrocytes ($CD45^-CD235^+$), and lymphoid cells ($CD45^+CD7^+$). It is also noted that this iMDSC population is significantly skewed towards a particular cell subtype, namely monocytic MDSCs (M-iMDSCs; $CD45^+CD33^+CD14^+$), with more than half of the population being M-iMDSCs. This contrasts with the MDSCs differentiated from primary $CD34^+$ cells (isolated from PBMC), where the obtained MDSC population comprises a maximum of 20% enrichment of CD33/CD14 cells (Casacuberta-Serra et al., 2017), indicating an even lower percentage of monocytic MDSCs.

In addition, over 50% of iMDSCs obtained herein express elevated levels of PD-L1 compared to only 20% in the MDSC population derived from primary $CD34^+$ cells in the same referenced study. PD-L1, also known as B7-H1, is a potent transmembrane immune checkpoint protein that belongs to the B7 family of T cell co-inhibitory molecules. PD-L1 has been described in cancer immunotherapy for its role in blocking T cell activation and proliferation. More specifically, PD-L1 is capable of preventing T cell activation through competition for costimulatory molecules on the T cell (e.g. B7-1 and/or B7-2) and through direct engagement of PD1 on the T cell. Therefore, PD-L1 is capable of regulating T-cell activation in a cell contact dependent fashion. The binding of PD-L1 to its receptor PD-1 dampens T cell activation, decreases proliferation and cytotoxicity, and induces apoptosis. Therefore, the iMDSC population comprising increased number and ratio of cell subpopulations that express PD-L1 is desirable for its enhanced immuno-regulatory property further described in the following examples.

Figure 1F:
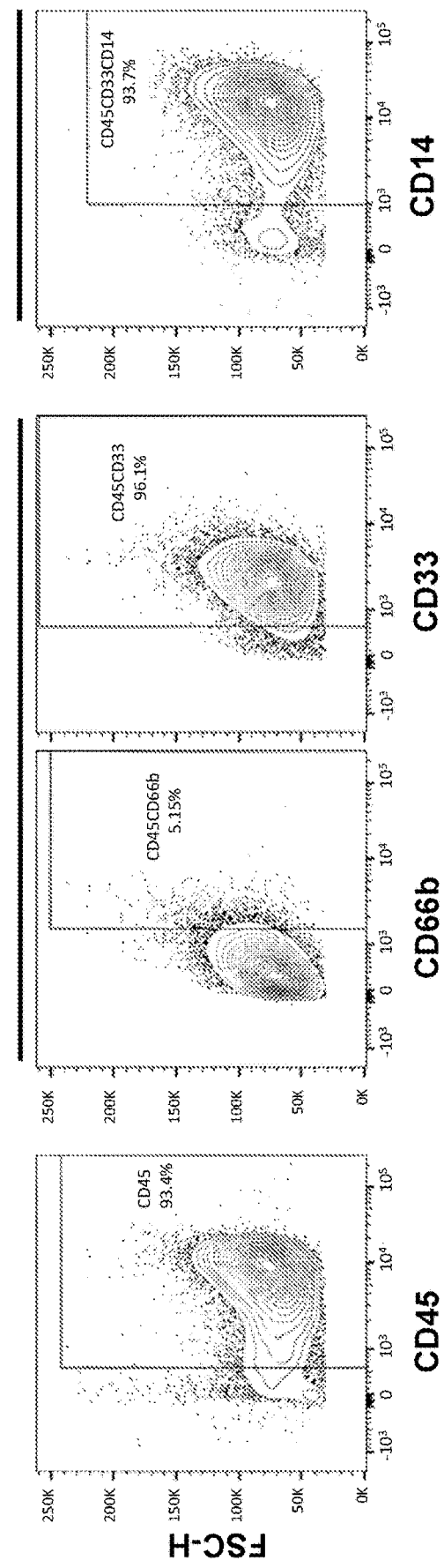

The process provided herein for making iPSC derived MDSCs having enhanced immuno-regulatory property is also proven to be robust and scalable, enabling the production of over 1,000 iMDSCs for 1 iPSC (FIG. 1E). As an effort to optimize the selective differentiation and expansion of iMDSC, at 12 days post seeding of iCD34, the cells were collected and re-plated and grown for a further 3 days in myeloid differentiation media. As shown in FIG. 1F, this extension in the differentiation process resulted in a significant increase in the subpopulation of monocytic MDSCs (having pheonotype $CD45^+$, $CD33^+$, and $CD14^+$) from above 50% in an approximate 9-day process to above 90% in an extended process of about 15 days, with the maximal expansion appear around 12 days post seeting of the iCD34 cells. With this extended differentiation process, at day 10+15, some monocytic MDSCs also express early markers of macrophages such as CD206, and early markers of dendritic cells such as CD11c. It is therefore expected that extending the culture of monocytic MDSCs behond day 15 post iCD34 seeding, without changing the cytokine composition of the media, it is likely to yield more mature macrophages, which are further characterized by for example, CD163, CD86, and/or CD68 expression. Similarly, addition of increasing concentrations of IL4 to the day 10+15 differention media would expectedly promote differentiation of monocytic MDSCs to dendritic cells.

The results also show that a cytokine cocktail without IL6 favors expansion of iMDSCs under culture conditions such as StemPro-34. The differentiation and expansion of iMDSCs from iPSCs using the composition and methods of the present application does not require feeder cells. When feeder cells are used, they may include endothelial cells, stromal cells (for example, epithelial cells or fibroblasts), or leukemic cells. Specific examples of feeder cells include, but are not limited to, OP9 or K562, or their engineered variants thereof.

Figure 2A:
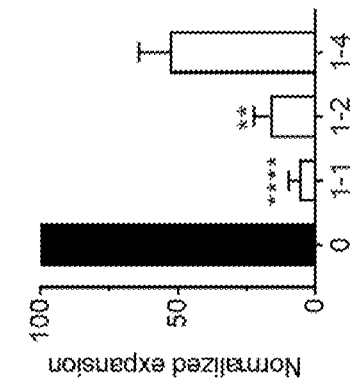
FIGS. 2A-C shows the in vitro T cell suppression assay of the iMDSCs. T cell expansion for independent donors following iMDSCs co-culturing was quantified and reveals significant and titratable reductions in T cell expansion independent of HLA matching.
Figure 2A:
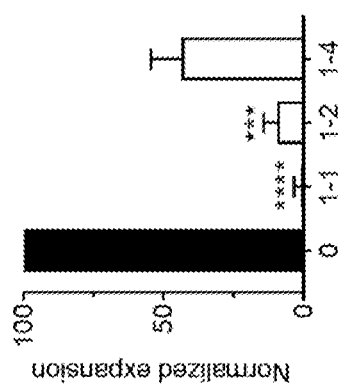
Figure 2B:
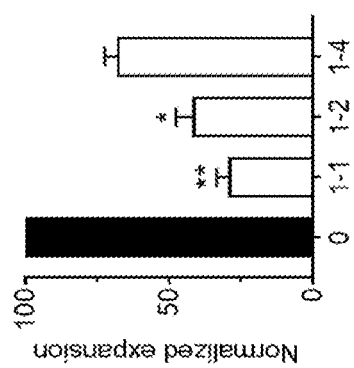
Figure 2B:
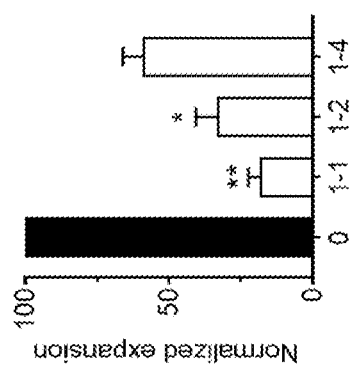
Figure 2C:
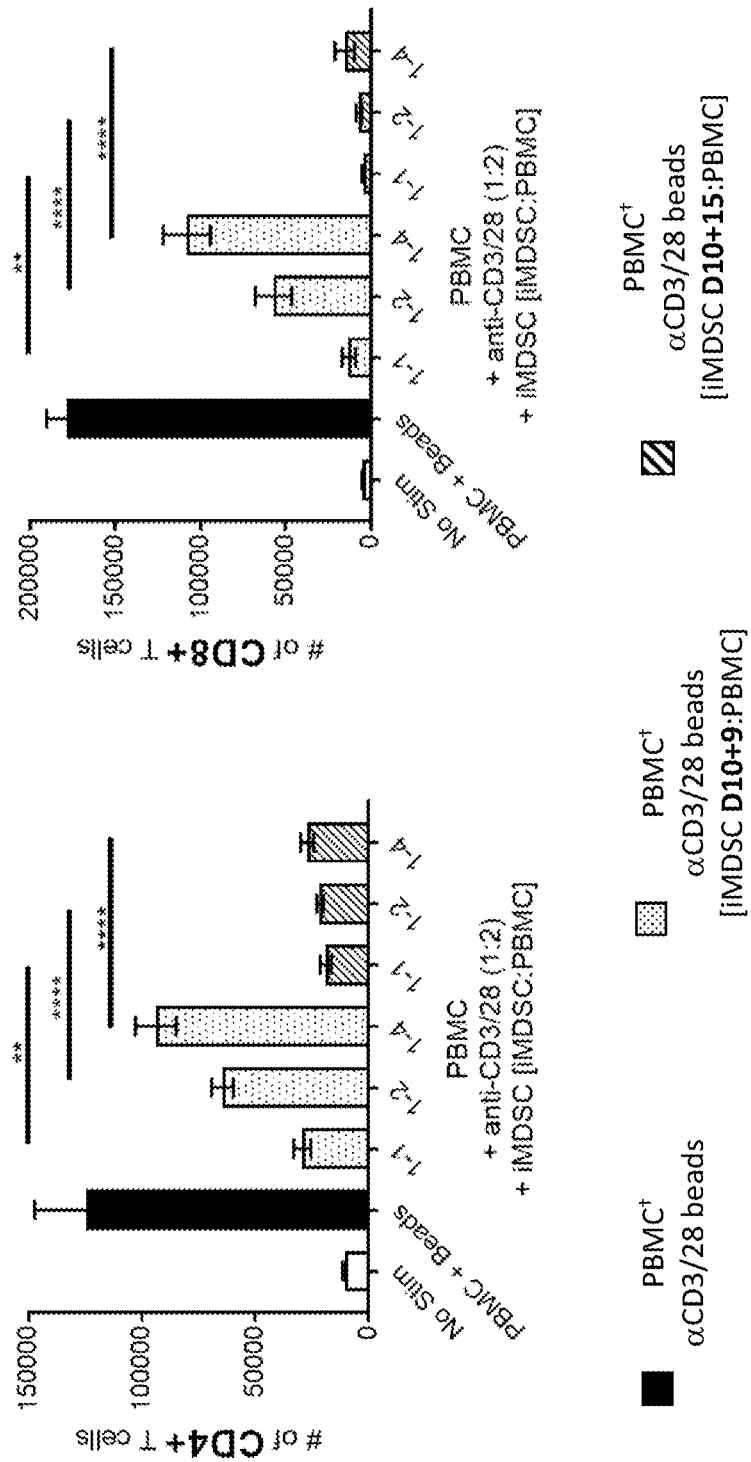

Example 2—iMDSCs Potently Suppressed T Cell Proliferation and Effector Function Independently of HLA Matching To evaluate the functionality of iMDSCs, $5 \times 10^4$ previously frozen and banked ficoll-separated PBMCs from each of 5 independent donors were rested overnight, labeled with Cell Trace Violet (Invitrogen, Carlsbad, CA), and activated with anti-CD3/28 beads (ThermoFisher) at a ratio of 1:2. iMDSCs were co-cultured with activated PBMCs at a ratio of 1:1, 1:2, or 1:4 in complete RPMI medium in 96-well U bottom plates. Five days later co-cultures were harvested and T cell expansion was quantified via flow cytometry. PBMC/iMDSC co-cultures were washed, stained with Live/Dead Fixable Near-IR viability dye (eBioscience) to exclude dead cells, FC-blocked (BD Biosciences, San Diego, CA) for about 30 minutes on ice, and surface stained for about 30 minutes on ice with fluorescently conjugated antibodies (BD Biosciences and Biolegend, San Diego, Ca) to CD3 (UCHT1), CD14 (M5E2), CD8α (RPA-T8), and CD4 (RPA-T4). T cells were identified as Viability Dye-$CD3^+CD14^-$ and either $CD8α^+$ or $CD4^+$. After staining, cells were washed three times and acquired on a LSR-Fortessa (BD Biosciences) and analyzed with FlowJo v10 (Treestar, Ashland, OR)). Relative T cell numbers were determined using AccuCount Fluorescent beads (Spherotech Lake Forest, IL). T cell expansion following iMDSCs coculture was then quantified for five independent donors and reveals significant and titratable reductions in T cell expansion independent of HLA matching (FIG. 2). As shown in FIG. 2A, coculturing with iMDSCs reduced T cell expansion by up to about 75-85%. T cell suppression activity of iMDSCs differentiated using the extended protocol (for example, D10+15) is shown in FIG. 2B. The D10+15 iMDSCs were co-cultured with T cells activated with CD3/CD28. T cell expansion following iMDSCs co-culturing was quantified by flow cytometry for three independent donors of T cells and reveals significant and titratable reductions in T cell expansion independent of HLA matching (all data are presented as averages +/−SEM. **$p<0.0001$, *$p<0.001$ and **$p<0.01$). These results show that increased number and proportion of monocytic MDSCs in the iMDSC population correlates with an enhanced capacity of MDSCs to suppress T cells.

Further, to evaluate iMDSCs' T cell suppressive activity, the iMDSCs obtained 9 or 15 days after D10 THE were co-cultured with T cells activated with CD3/CD28. As shown above, extending differentiation of iMDSCs using the D10+5 protocol significantly enhanced the T cell suppressive activity of iMDSC compared to iMDSCs differentiated using the D10+9 protocol (see FIG. 2C; all data are presented as averages +/−SEM. **$p<0.0001$ and $p<0.01$).

To evaluate iMDSCs' ability in impacting T cell effector function, cytokine production profiling in iMDSCs co-cultured T cells were investigated. For intracellular cytokine staining, after 5 days of co-culture with iMDSCs, activated PBMCs were reactivated with PMA/Ionomycin (eBioscience) for 4 hours in the presence of BrefeldinA (GolgiPlug, BD Biosciences) and PE-conjugated anti-CD107a (H4A3, BD Biosciences) antibodies. After stimulation, PBMC co-cultures were washed, stained with viability dye, Fc-Blocked, and surface stained for CD3, CD4, and CD8a for 30 minutes on ice. After surface staining, PBMCs were washed, fixed/permeablized with Cytofix/Cytoperm (BD Biosciences), and resuspended in 1× PermWash (BD Biosciences). Cytokine production was identified with antibodies (Biolegend) to IFNγ (4S.B3), TNF (Mab11), and IL2 (MQ1-17H12) for 30 minutes on ice. PBMC co-cultures were then washed with 1× PermWash, acquired on a LSR-Fortessa, and analyzed with FlowJo v10. Unstimulated PBMCs served as a control to identify specific cytokine production by the co-cultured T cells.

Figure 3A:
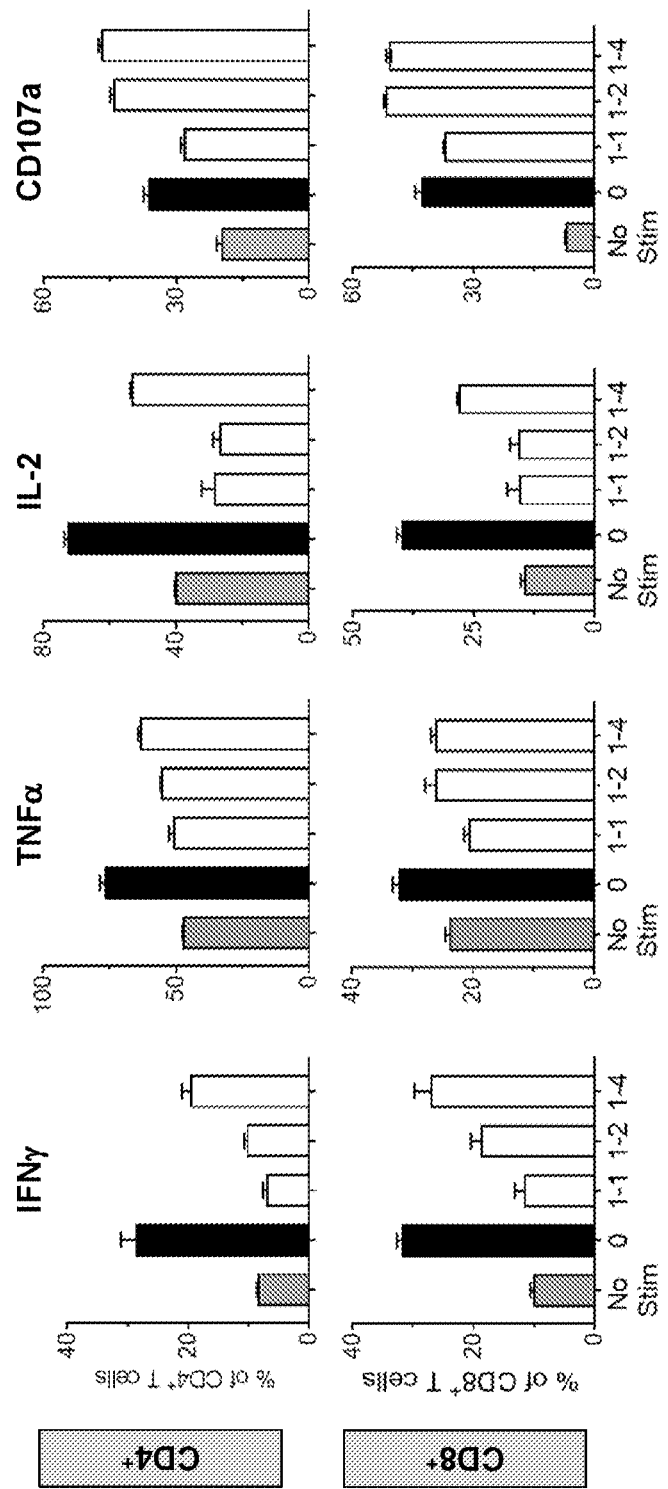
FIGS. 3A-B shows the in vitro cytokine release assay of the iMDSCs.
Figure 3B:
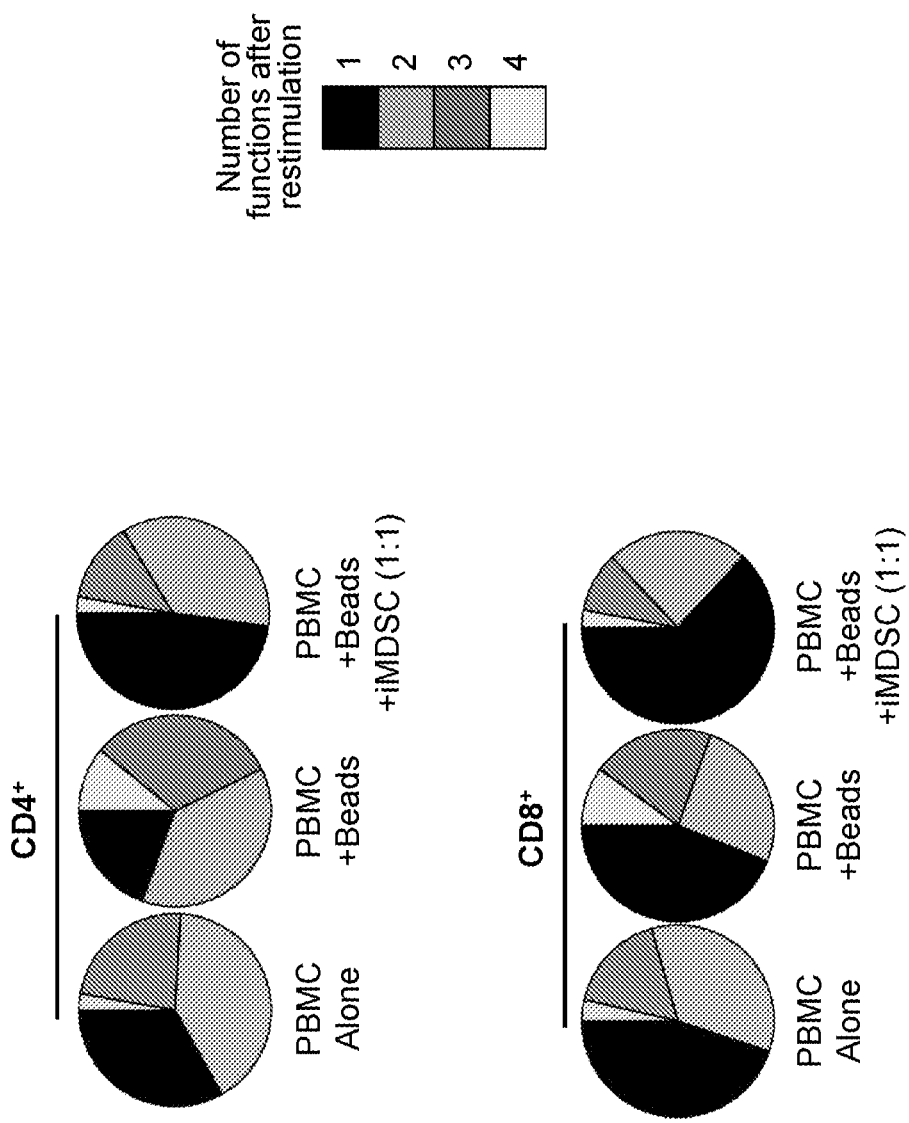

To determine whether iMDSCs inhibit T cell effector function, as evidenced by cytokine secretion and degranulation, five-day bead activated PBMCs and iMDSCs cocultures were restimulated with phorbol myristate acetate and ionomycin; and intracellular cytokine production and degranulation was assessed by flowcytometry. When cocultured with iMDSCs, both $CD4^+$ and $CD8^+$ T cells experienced deficits in their abilities to rapidly produce IFNγ, TNF, IL2, and to express CD107a, demonstrating that iMDSCs inhibit T cell effector function in addition to T cell proliferation (FIG. 3A). Moreover, T cell cocultured with iMDSCs are less capable of producing multiple effector functions (3 or 4 functions) and are mostly limited to one or two functions (FIG. 3B), indicating that co-culturing with iMD-SCs suppresses the T cell effector function despite the T cell stimulation and restimulation.

Example 3—iMDSCs Attenuates Graft Versus Host Disease (GvHD)

To assess iMDSCs ability in attenuating GvHD, autoimmune diseases, or inflammatory indications in vivo, a xenogeneic acute GvHD mouse model was used. All animal experiments were approved and conducted in accordance with internal Institutional Animal Care and Use Committee. NSG mice (JAX #005557) were sub lethally irradiated with 2Gy, and one day later intravenously injected with $7.5 \times 10^6$ overnight rested PBMCs. Half of the mice also received $2.5 \times 10^6$ iMDSCs along with the injected PBMCs. Symptoms of clinical GvHD in the animals were scored up to 50 days, and the weight and survival of the animals were also monitored during the same period. On day 14 after treatment, peripheral blood was collected, red blood cell lysed, and stained with fluorescently conjugated antibodies (BD Biosciences and Biolegend) to mCD45 (30-F11), hCD45 (2D1), hCD3, hCD4, hCD25 (M-A251), and hCD127 (A019D5) to quantify levels of human chimerism (hCD45$^+$ mCD45$^-$) and regulatory T cells (hCD45$^+$CD3$^+$CD4$^+$CD25$^+$ CD127$^{lo}$).

Figure 4B:
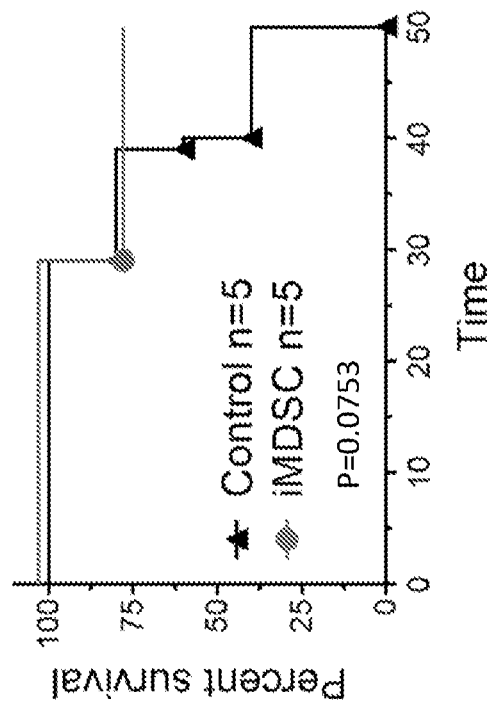
FIGS. 4A-C shows iMDSCs in vivo functional assay using the xenogeneic acute GvHD model.
Figure 4A:
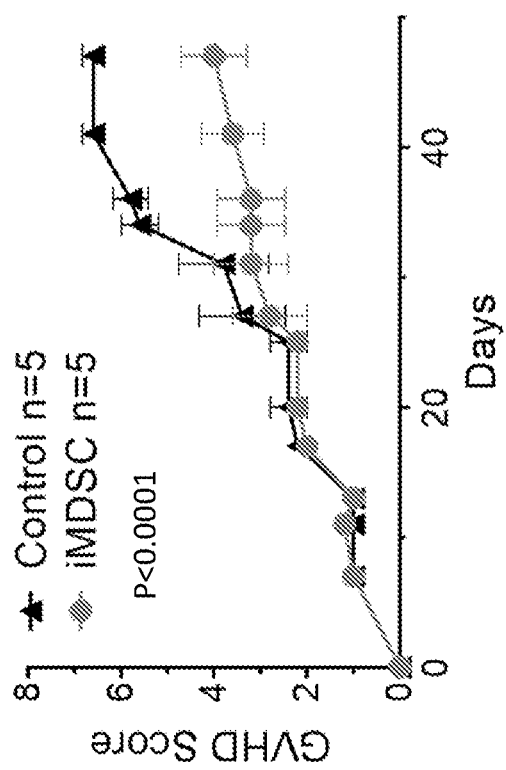
Figure 4C:
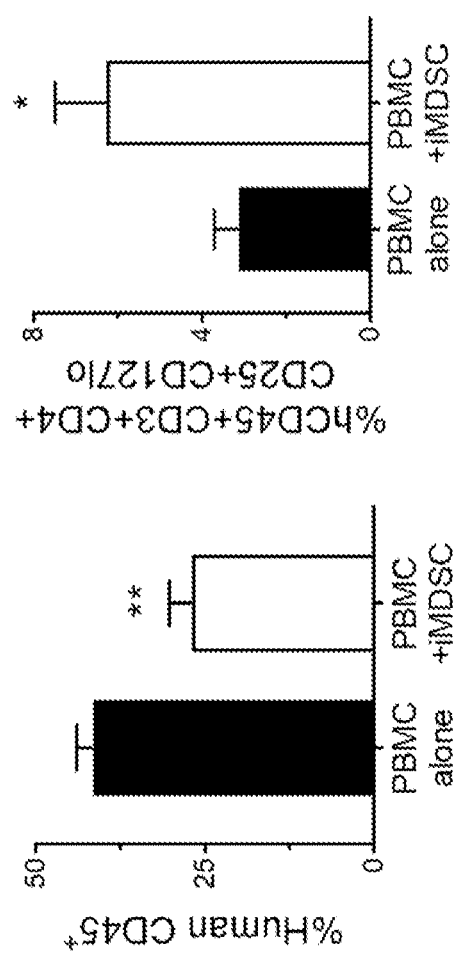

Clinical GvHD signs and symptoms including: diarrhea, inactivity, hunched posture, ruffled fur, eye lesion, snout swelling/skin integrity. Weight was monitored as an independent parameter correlating with disease course. as measured by GvHD score, FIG. 4A shows that a single iMDSC infusion significantly attenuated the severity of disease. Further, Kaplan-Meier survival curves were generated using disease endstage (loss of >25% of body weight) as the termination criteria. Attenuation of disease by iMDSC infusion also resulted in prolonged survival, thus demonstrating that iMDSCs are potent suppressors of T cells in an in vivo context of disease (FIG. 4B). Additionally, it was observed that iMDSCs led to a significant reduction in human CD45$^+$ expansion at day 14 with an increase in Tregs (CD4+ CD25$^{hi}$CD127$^{lo}$) in peripheral blood (FIG. 4C).

Example 4—iMDSCs Derived from Genetically Engineered iPSCs

Clonal iPSCs were engineered to overexpress PDL1, and were differentiated to iCD34 cells overexpressing the introduced PDL1 using the methods and compositions provided in this application. The modified iCD34 cells were differentiated into iMDSCs using the protocol provided herein, without evidence of disrupted cell developmental biology, and the resultant iMDSCs also overexpress PDL1 (iMDSCs-PDL1). iMDSCs (without PDL1 modification) and iMDSCs-PDL1 were co-cultured with T cells activated with CD3/CD28 and T cell expansion was assessed by flow cytometry. The results showed that overexpression of PDL1 did not negatively impact the T cell suppressive activity of iMDSCs in vitro. A test of iMDSCs-PDL1 in a xenogenic model of GvHD as described above provides in vivo confirmation of the efficacy of iMDSCs-PDL1 in comparison to iMDSC. An increased suppressive activity of iMDSCs in vivo attributed to increased PDL1 expression of the modified cells is expected based on earlier findings regarding MDSCs overexpressing PDL1 (see for example, Clements et al., 2018 J Leukoc Biol).

Further genetic modifications incorporated in the derivative iMDSCs of the application are related to immune evasion of the cells. In some embodiments, the iPSC are first engineered to comprise one or more of B2M null, HLA-E, HLA-G, PDL1, A2AR, CD47, LAG3 null, TIM3 null, TAP1 null, TAP2 null, Tapasin null, NLRC5 null, PD1 null, RFKANK null, CITTA null, RFX5 null and RFXAP null. The derivative hematopoietic cells, including iMDSCs, differentiated from said engineered iPSC comprise the same engineered modalities relating to HLA class I and/or II as the iPSC. These cells with modified HLA class I and/or II have increased resistance to immune detection, and therefore present improved in vivo persistence. Moreover, such cells can avoid the need for HLA matching in adoptive cell therapy and thus provide a source of universal, off-the-shelf therapeutic regimen. As an example, iCD34+ cells and iCD34+ cells deficient in B2M expression with/without overexpressing HLA-G were differentiated into iMDSCs using the extended differentiation and expansion protocol. iMDSCs (Control), iMDSCs deficient in B2M expression (B2M KO) and iMDSCs deficient in B2M expression and overexpressing HLAG (HLAG B2M KO) were co-cultured with T cells activated with CD3/CD28 and T cell expansion was assessed by flow cytometry. The results show that B2M deficiency alone or together with HLA-G overexpression did not decrease the T cell suppressive activity of iMDSCs. This suggests that attenuating immunogenicity of iMDSCs by eliminating HLA class 1 expression and expressing the immune-regulatory protein HLA-G is a viable strategy to enhance persistence of iMDSCs without compromising the immune-regulatory activity of the cells. The persistence of iMDSCs engineered for immune evasion is further confirmed in a xenogenic model of GvHD in a comparison to iMDSC.

One skilled in the art would readily appreciate that the methods, compositions, and products described herein are representative of exemplary embodiments, and not intended as limitations on the scope of the invention. It will be readily apparent to one skilled in the art that varying substitutions and modifications may be made to the present disclosure disclosed herein without departing from the scope and spirit of the invention.

All patents and publications mentioned in the specification are indicative of the levels of those skilled in the art to which the present disclosure pertains. All patents and publications are herein incorporated by reference to the same extent as if each individual publication was specifically and individually indicated as incorporated by reference.

The present disclosure illustratively described herein suitably may be practiced in the absence of any element or elements, limitation or limitations that are not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the present disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. An in vitro method of generating a population of induced immune regulatory cells, comprising:
   (i) obtaining induced definitive hemogenic endothelium cells (iHE); and
   (ii) directing differentiation of iHE with a medium composition comprising a ROCK inhibitor, GMCSF, and MCSF;
   thereby generating a population of induced immune regulatory cells comprising induced myeloid suppressive cells, wherein the induced myeloid suppressive cells are $CD45^+$ and $CD33^+$;
   and wherein the cell population has enhanced therapeutic potential.

2. The method of claim 1, wherein:
   a) the medium composition further comprises (1) one or more growth factors and cytokines selected from the group consisting of IL1b, IL3, IL6, IL4, IL10, IL13, TGFβ, bFGF, VEGF, SCF, and FLT3L, and optionally, (2) one or both of an AhR antagonist and a prostaglandin pathway agonist;
   b) the medium composition is feeder-free, and/or serum-free;
   c) the population of induced myeloid suppressive cells comprise induced myeloid-derived suppressor cells (iMDSs);
   d) the population of induced immune regulatory cells comprises a subpopulation of: (i) monocytic MDSCs (M-MDSCs); (ii) $CD45^+CD33^+CD14^+$ cells; (iii) $CD45^+CD33^+PDL1^+$ cells; (iv) granulocytic MDSCs (G-MDSCs); (v) $CD45^+CD14^-CD15^+CD11b^+$ cells; (vi) $CD45^+CD206^+$ cells; or (vii) $CD45^+CD11c^+CD14^-HLADR^{high}$ cells;
   e) the population of induced immune regulatory cells comprises:
      (1) more than 90% of iMDSCs, wherein the iMDSCs comprise monocytic MDSCs;
      (2) more than 20%, 30%, 40%, 50%, 60%, 70%, 80%, or 90% of monocytic MDSCs, and/or $CD45^+CD33^+PDL1^+$ cells; wherein the monocytic MDSCs comprise $CD45^+CD33^+CD14^+$ cells; and/or
      (3) more than 20%, 30%, 40% or 50% of granulocytic MDSCs, wherein the granulocytic MDSCs comprise $CD45^+CD11b^+CD14^-CD15^+$ cells; and/or
      (4) more than 20%, 30%, 40% or 50% of macrophages; wherein the macrophages comprise $CD45^+CD206^+$ cells; and/or
      (5) more than 20%, 30%, 40% or 50% of dendritic cells; wherein the dendritic cells comprise $CD45^+CD11c^+CD14^-HLADR^{high}$ cells;
   f) the population of induced immune regulatory cells comprises iMDSCs and is essentially free of granulocytes, erythrocytes, and/or lymphoid cells;
   g) the induced myeloid suppressive cells comprised in the population of induced immune regulatory cells comprise one or more genetic imprints obtained from genetically engineering the induced myeloid suppressive cells;
   h) the induced myeloid suppressive cells comprised in the population of induced immune regulatory cells comprise one or more genetic imprints retained from iHE comprising the same genetic imprint(s);
   i) the iHE cells are derived from induced pluripotent stem cells (iPSC), iPSC derived mesodermal cells, or iPSC derived mesodermal cells with definitive hemogenic endothelium potential; and optionally the iPSC comprises one or more genetic imprints retainable by its derived cells;
   j) the ROCK inhibitor is thiazovivin or Y27632; or
   k) the enhanced therapeutic potential comprises (1) increased number or ratio of induced MDSCs in the induced immune regulatory cell population; (2) improved potency in suppressing T cell proliferation and effector function; or (3) ability in attenuating GvHD,
   as compared to myeloid suppressive cells comprised in PBMC (peripheral blood mononuclear cell).

3. The method of claim 2, wherein:
   a) the AhR antagonist comprises StemRegenin1 (SR1);
   b) the one or more genetic imprints of iPSC are obtained by a method comprising: (i) obtaining a source specific immune cell that is donor-, disease-, or treatment response-specific, wherein the immune cell presents retainable therapeutic attributes; and (ii) reprogramming the source specific immune cell to iPSC; or by a method comprising genomic editing during or after reprogramming a non-pluripotent cell to iPSC, wherein the genetic imprint comprises one or more genetically modified modalities introduced through genomic insertion, deletion or substitution in the genome of the iPSC;
   c) the method further comprises genomic editing of the induced myeloid suppressive cells through genomic insertion, deletion or substitution in the genome of the induced myeloid suppressive cells to introduce one or more genetically modified modalities to the cells; or
   d) the method further comprises modulating the induced myeloid suppressive cells of by contacting one or more modulating agents to enhance therapeutic potential of the cells.

4. The method of claim 3, wherein the genetically modified modalities comprise:
   a) one or more of: safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the induced myeloid suppressive cells or one or more of the subpopulations thereof,
   b) introduced or increased expression of a chimeric receptor, a homing receptor, an anti-inflammatory molecule, an immune checkpoint protein, a cytokine/chemokine decoy receptor, a growth factor, an altered proinflammatory cytokine receptor, a CAR, or a surface triggering receptor for coupling with bi- or multi-specific or universal engagers; and optionally, wherein the introduced or increased expression is driven by a promoter regulated by inflammatory signaling; and/or
   c) reduced or silenced expression of a co-stimulatory gene.

5. The method of claim 4, wherein:
   a) the genetically modified modalities comprise (i) deletion or reduced expression of B2M, TAP1, TAP2, Tapasin, NLRC5, RFXANK, CITTA, RFX5, RFXAP, or any of the HLA genes in the chromosome 6p21 region; or (ii) introduced or increased expression of IDO1, PDL1, CTLA4, Arg1, IL35, IL10, HO-1, CrmB, Y136, HGFL, GMCSF, TGFβ, HLA-E, HLA-G, CAR, or surface triggering receptors for bi- or multi-specific engagers;

b) the chimeric receptor comprises (i) an extracellular domain comprising an antigen specific binding sequence, an immunoglobulin, or a pro-inflammatory cytokine receptor; and (ii) an intracellular domain for anti-inflammatory signaling comprising at least one of IL10R, IL35R, and AhR;
c) the homing receptor or adhesion molecule comprises CXCR4, CCR2, CCR5, CCR6, CXCR3, CCR7, CD62L, or VLA4;
d) the promoter (i) is a promoter driven by inflammatory signaling comprising TLR or IFNγR signaling; (ii) is an inducible promoter; and/or (iii) is triggered only after homing of the iMDSCs;
e) the altered pro-inflammatory cytokine receptor (i) sequesters pro-inflammatory cytokines comprising IL2R, IL6R, or IFNγR; (ii) is membrane bound; or (iii) is in a soluble form; or
f) the bi- or multi-specific engager is specific to one or more tumor-specific antigen on the surface of a tumor cell.

6. The method of claim 3, wherein the therapeutic attributes of the source specific immune cell comprise one or more of (i) antigen targeting receptor expression; (ii) HLA presentation or lack thereof, (iii) resistance to tumor microenvironment; (iv) induction of bystander immune cells and immune modulations; (iv) improved on-target specificity with reduced off-tumor effect; (v) resistance to treatment such as chemotherapy; and (vi) improved homing, persistence, and cytotoxicity.

7. The method of claim 2, wherein deriving iHE cells from induced pluripotent stem cells (iPSC) further comprises differentiating iPSCs to mesodermal cells; differentiating iPSC derived mesodermal cells to mesodermal cells with definitive hemogenic endothelium potential; and differentiating iPSC derived mesodermal cells with definitive hemogenic endothelium potential to iHE.

8. The method of claim 7, wherein differentiating iPSC derived mesodermal cells with definitive hemogenic endothelium potential to iHE comprises: contacting the mesodermal cells having definitive HE potential with a composition comprising bFGF and a ROCK inhibitor to obtain definitive HE cells;
wherein differentiating iPSC derived mesodermal cells to mesodermal cells with definitive hemogenic endothelium potential comprises: contacting the iPSC derived mesodermal cells with a composition comprising a BMP activator, a GSK3 inhibitor and bFGF to obtain the mesodermal cells having definitive HE potential;
wherein differentiating iPSCs to mesodermal cells comprises contacting the iPSCs with a composition comprising a BMP activator, and optionally a bFGF to obtain iPSC derived mesodermal cells; and optionally,
wherein the iPSCs are seeded and expanded in a composition comprising a ROCK inhibitor, a GSK3 inhibitor and a MEK inhibitor, and wherein the composition is free of TGFβ receptor/ALK inhibitors.

9. The method of claim 8, wherein the differentiation of iPSC is (i) void of the step of generating embryoid bodies; (ii) under monolayer culturing; (iii) under feeder-free condition; and/or (iv) under stromal-free condition.

10. The method of claim 2, further comprising isolating the induced myeloid suppressive cells that are CD45$^+$ and CD33$^+$ or one or more subtypes thereof.

11. The method of claim 1, wherein the medium composition further comprises one or more of VEGF, bFGF, SCF, IL3, FLT3L, and an AhR antagonist.

12. The method of claim 11, wherein the medium composition comprises the ROCK inhibitor, MCSF, VEGF, bFGF, SCF, IL3, FLT3L, GMCSF, and the AhR antagonist.

* * * * *

UNITED STATES PATENT AND TRADEMARK OFFICE
CERTIFICATE OF CORRECTION

PATENT NO. : 11,851,677 B2
APPLICATION NO. : 16/622237
DATED : December 26, 2023
INVENTOR(S) : Philippe A. Parone et al.

Page 1 of 1

It is certified that error appears in the above-identified patent and that said Letters Patent is hereby corrected as shown below:

In the Claims

Column 43, Line 27, in the twelfth line of Claim 2, delete "(IMDSs);" and insert --(iMDSCs);--

Signed and Sealed this
Fourth Day of February, 2025

Coke Morgan Stewart
*Acting Director of the United States Patent and Trademark Office*